(12) United States Patent
Young et al.

(10) Patent No.: US 6,362,003 B1
(45) Date of Patent: *Mar. 26, 2002

(54) HEMATOLOGICAL REFERENCE CONTROL COMPOSITION CONTAINING LEUKOCYTE ANALOGS, METHODS OF MAKING, AND USES THEREOF

(75) Inventors: Carole Young, Miami; Michael Elliott, Cooper, both of FL (US); Nancy Naylor, Waverly, PA (US); Timothy J. Fischer, Raleigh, NC (US)

(73) Assignee: Coulter Corporation, Miami, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/152,262

(22) Filed: Sep. 14, 1998

Related U.S. Application Data

(63) Continuation of application No. 08/787,408, filed on Jan. 22, 1997, which is a continuation of application No. 08/432,435, filed on Apr. 28, 1995, now abandoned, which is a continuation-in-part of application No. 08/386,711, filed on Feb. 8, 1995, now Pat. No. 5,529,933, which is a continuation of application No. 08/081,529, filed on Jun. 23, 1993, now abandoned, which is a continuation of application No. 07/840,438, filed on Feb. 24, 1992, now abandoned.

(51) Int. Cl.[7] .................. G01N 31/00; G01N 33/48
(52) U.S. Cl. ..................... 436/10; 436/13; 436/15; 436/16; 436/17; 436/18; 436/63; 424/532; 424/533; 424/534
(58) Field of Search .................. 436/8, 10, 13, 436/15–18, 63; 424/532–534

(56) References Cited

U.S. PATENT DOCUMENTS

| | | | |
|---|---|---|---|
| 2,656,508 A | 10/1953 | Coulter | |
| 3,341,411 A | 9/1967 | Campbell et al. | |
| 3,502,974 A | 3/1970 | Coulter et al. | 324/71 |
| 3,558,522 A * | 1/1971 | Louderback et al. | 436/10 |
| 3,574,137 A * | 4/1971 | Decasperis | 436/10 |
| 3,632,735 A * | 1/1972 | Kita | 436/10 |
| 3,672,954 A | 6/1972 | Grippa | |
| 3,698,998 A | 10/1972 | Avrillon | |
| 3,741,875 A | 6/1973 | Ansley et al. | 195/103 R |
| 3,799,743 A | 3/1974 | Alexander et al. | |
| 3,836,849 A | 9/1974 | Coulter et al. | 324/71 |
| 3,873,467 A * | 3/1975 | Hunt | 252/408 |
| 4,202,033 A | 5/1980 | Strobel | 364/416 |
| 4,213,876 A | 7/1980 | Crews et al. | 252/408 |
| 4,219,440 A | 8/1980 | Runck et al. | 436/10 |
| 4,250,051 A * | 2/1981 | Armstrong | 436/15 |
| 4,264,470 A | 4/1981 | Chastain, Jr. et al. | 252/408 |
| 4,290,774 A | 9/1981 | Girgis et al. | 252/408 |
| 4,299,726 A | 11/1981 | Crews et al. | 252/408 |
| 4,309,184 A | 1/1982 | Ali | |
| 4,358,394 A | 11/1982 | Crews et al. | 252/408 |
| 4,389,490 A | 6/1983 | Crews et al. | 436/17 |
| 4,390,632 A * | 6/1983 | Carter, II | 436/10 |
| 4,405,719 A | 9/1983 | Crews et al. | 436/10 |
| 4,436,821 A * | 3/1984 | Ryan | 436/10 |
| 4,485,175 A | 11/1984 | Ledis et al. | 436/63 |
| 4,526,715 A | 7/1985 | Kothe et al. | |
| 4,579,824 A | 4/1986 | Louderback et al. | 436/10 |
| 4,622,294 A | 11/1986 | Kung et al. | |
| 4,652,257 A | 3/1987 | Chang | |

(List continued on next page.)

FOREIGN PATENT DOCUMENTS

| | | |
|---|---|---|
| CH | 579 148 | 2/1973 |
| EP | 0 201 390 | 4/1986 |
| EP | 0 216 481 | 8/1986 |
| EP | 0 242 135 | 4/1987 |
| EP | 0 300 682 | 7/1988 |
| EP | 0 311 163 | 9/1988 |
| EP | 0 337 492 | 4/1989 |
| GB | 1509539 * | 5/1978 |
| JP | 63-163164 | 7/1963 |
| JP | 2-286097 | 11/1990 |
| JP | 2-286098 | 11/1990 |
| SU | 1141336 A | 12/1982 |
| SU | 1481687 A1 | 4/1985 |
| WO | WO 80/01515 | 1/1980 |
| WO | WO/89/12682 | 6/1989 |

OTHER PUBLICATIONS

A.J.P.F. Lombarts et al. Clin. Chim. Acta 1983, 129, 79–83.*

A.J.P.F. Lombarts et al. Clin. Chim. Acta 1983, 130, 95–102.*

A.J.P.F. Lombarts et al. Ann. Clin. Biochem. 1983, 20, 302–307.*

A.J.P.F. Lombarts et al. Clin. Chim. Acta 1984, 139, 145–154.*

(List continued on next page.)

Primary Examiner—Arlen Soderquist
(74) Attorney, Agent, or Firm—Finnegan, Henderson, Farabow, Garrett & Dunner, L.L.P.

(57) ABSTRACT

A method of quality control to diagnose the cause of a malfunction of an instrument. The method uses measurements of the physical property of a sample to diagnose the cause of a malfunction of an instrument. The spatial position of a control product sample is analyzed. Alternatively, the spatial position of a statistically significant number of patient blood samples can be used. The method enables the monitoring of an instrument for problems associated with debris and noise caused by red cell lysis inefficiency; instrument reagents pump volume settings; instrument laser alignments; instrument gain settings; and flow noise caused by partial plugs, residual plugs or other flow problems. The method provides a more specific indication of the type and cause of an instrument malfunctioning than non specific flagging provided by prior art methods.

8 Claims, 2 Drawing Sheets

U.S. PATENT DOCUMENTS

| | | | |
|---|---|---|---|
| 4,683,293 A | 7/1987 | Craig | |
| 4,683,294 A | 7/1987 | Van Wijnendaele et al. | |
| 4,698,312 A | 10/1987 | Wong et al. | 436/10 |
| 4,704,364 A | 11/1987 | Carver et al. | 436/10 |
| 4,707,441 A | 11/1987 | Ahmad et al. | |
| 4,713,324 A | 12/1987 | Fox et al. | |
| 4,722,842 A | 2/1988 | Stallcup et al. | |
| 4,731,324 A | 3/1988 | Huang et al. | |
| 4,745,074 A | 5/1988 | Schreier et al. | |
| 4,751,179 A | 6/1988 | Ledis et al. | 435/34 |
| 4,777,139 A | 10/1988 | Wong et al. | 436/18 |
| 4,783,400 A | 11/1988 | Canova-Davis et al. | |
| 4,812,314 A | 3/1989 | Berenholz et al. | |
| 4,839,277 A | 6/1989 | Sugahara et al. | |
| 4,857,451 A | 8/1989 | Schwartz | 436/10 X |
| 4,858,154 A | 8/1989 | Anderson et al. | 364/554 |
| 4,873,088 A | 10/1989 | Mayhew et al. | |
| 4,886,813 A | 12/1989 | Nakamura et al. | |
| 4,897,381 A | 1/1990 | della Valle et al. | |
| 4,971,916 A | 11/1990 | Jou et al. | |
| 5,008,201 A | 4/1991 | Ryan | 436/10 |
| 5,262,327 A | 11/1993 | Ryan | |
| 5,270,208 A | 12/1993 | Ryan | |
| 5,320,964 A * | 6/1994 | Young et al. | 436/10 |
| 5,320,965 A | 6/1994 | Chiang | 436/11 |
| 5,342,754 A | 8/1994 | Maples et al. | 435/2 |
| 5,380,663 A | 1/1995 | Schwartz et al. | 436/10 |
| 5,380,664 A | 1/1995 | Carver et al. | 436/10 |
| 5,512,485 A | 4/1996 | Young et al. | 436/10 |
| 5,529,933 A | 6/1996 | Young et al. | 436/10 |
| 5,672,474 A * | 9/1997 | Ryan | 436/8 |
| 5,677,145 A * | 10/1997 | Ryan | 436/10 |
| 5,731,205 A | 3/1998 | Ryan | |

OTHER PUBLICATIONS

Cheetham et al., "Cholesterol Sulfate Inhibits the Fusion of Sendai Virus to Biological and Model Membranes," *The Journal of Biological Chemistry*, vol. 265, No. 21 pp. 12404–12409, Jul. 25, 1990.

Schlosser, "Sterol Dependent Membranelytic Action of Saponins," *Phytopathz*, vol. 74, pp. 91–94, 1972.

Tatsumi, "Alternations of Saponin Hemolysis during Storage of ACD Blood," *Vox Sanguinis*, vol. 41, No. 1, pp. 18–24, 1981.

Kanakaraj et al., "Influence of hypercholesterolemia on morphological and rheological characteristics of erythrocytes," *Atherosclerosis*, vol. 76, pp. 209–218, Apr. 1989.

Ojcius et al., "Characterization of the Inhibitory Effect of Lysolipids on Perforin–Mediated Hemolysis," *Molecular Immunology*, vol. 27, No. 3, pp. 257–261, Mar. 1990.

Kamber et al., "Alterations in the Activities of Rabbit Erthrocyte Membrane–Bound Enzymes Induced by Cholesterol Enrichment and Depletion Procedures," *Biosciences*, vol. 41c, No. 3, pp. 301–309, Mar. 1986.

Schroeder et al., "Membrane Cholestrol Dynamics: Cholesterol Domains and Kinetic Pools," *Proceedings of the Society for Experimental Biology and Medicine*, vol. 196, No. 3, pp. 235–252, Mar. 1991.

Davis et al., "Regulation of Cholesterol Synthesis and the Potential for its Pharmacologic Manipulation," *Pharmac. Ther*, vol. 43, pp. 221–236, 1989.

Yeagle, "Cholesterol and the cell membrane," *Biochimica et Biophysica Acta*, vol. 822, pp. 267–287, 1985.

Shinitzky, "An Efficient Method for Modulation of Cholesterol Level in Cell Membranes," *FEBS Letters*, vol. 85, No. 2, pp. 317–320, Jan. 1978.

Needham et al., "Elastic deformation and failure of lipid bilayer membranes containing cholesterol," *Biophysical Journal*, vol. 58, pp. 997–1009, Oct. 1990.

Nishikawa et al., "Interaction of Digitonin and Its Analogs with Membrane Cholesterol," *The Journal of Biochemistry*, vol. 96, No. 4, Oct. 1984, pp. 1231–1239.

Tatsumi et al., "The Contribution of Saponin Hemolysis in Observing Membrane Properties of Erythrocytes," *ACTA Haematologica Japonica*, vol. 45, No. 1, Feb. 1982, pp. 31–37.

Yamanaka et al., "Mechanism of Haemolysis by *Vibrio vulnificus* Haemolysin," *Journal of General Microbiology*, vol. 133, Part 10, Oct. 1987, pp. 2859–2864.

Schindler et al., "Serum Lipoproteins Protect Isolated Erythrocytes against Retinol–Induced Haemolysis," *International Journal for Vitamin and Nutrition Research*, vol. 55, Apr. 16, 1985, pp. 253–262.

Innis, "Alteration of Erythrocyte Lipid Composition following Total Parenteral Nutrition in the Rat," *Journal of Parenteral and Enteral Nutrition*, vol. 13, No. 1, Jan. 1989, pp. 47–50.

Yorio et al., "Phospholipids and Electrolyte Transport," *Proceedings Of The Society For Experimental Biology And Medicine*, vol. 195, No. 3, Dec. 1990, pp. 293–303.

Shiao et al., "The solubilization and morphological change of human platelets in various detergents," *Biochimica et Biophysica Acta*, vol. 980, No. 1, Mar. 27, 1989, pp. 56–68.

Canicatti, "Hemolysins: Pore–forming proteins in invertebrates," *Experientia*, vol. 46, No. 3, Mar. 15, 1990, pp. 239–244.

Gonzalez–Manas et al., "The interaction of Triton X–100 with purple membranes," *European Journal of Biochemistry*, vol. 188, No. 3, Mar. 1990, pp. 673–678.

Bangham et al., "Action of Saponin on Biological Cell Membranes," *Nature*, vol. 196, No. 4858, Dec. 8, 1962, pp. 952–953.

Nakamura et al., "Interaction Of Saponins With Red Blood Cells As Well As With The Phosphatidylcholine Liposomal Membranes," *Journal of Pharmacobio–Dynamics*, vol. 2, No. 6, Nov. 1979, pp. 374–382.

DiGiulio et al., "PPIX Induced Photohemolysis Of Erythrocytes Partially–Depleted Of Cholesterol," *Biochemistry International*, vol. 19, No. 1, Jul. 1989, pp. 19–25.

Westerman et al., "Erythrocyte lipids: A comparison of normal young and normal old populations," *The Journal of Laboratory and Clinical Medicine*, vol. 62, No. 3, Sep. 1963, pp. 394–400.

Segal et al., "On The Mechanism Of Saponin Hemolysis–I," *Biochemical Pharmacology*, vol. 23, No. 5, Mar. 1, 1974, pp. 973–981.

Segal et al., "On The Mechanism Of Saponin Hemolysis–II," *Biochemical Pharmacology*, vol. 24, No. 1, Jan. 1, 1975, pp. 77–81.

Segal et al., "Effect Of Ester Groups On The Haemolytic Action Of Sapogenins–II," *Biochemical Pharmacoogy*, vol. 19, No. 8, Aug. 1970, pp. 2501–2507.

Ohno–Iwashita et al., "Protease–nicked 0–toxin of *Clostridium perfringens*, a new membrane probe with no cytolytic effect, reveals two classes of cholesterol as toxin––binding sites on sheep erythrocytes," *European Journal of Biochemistry*, vol. 176, No. 1, Sep. 1988, pp. 95–101.

Linder et al., "Cytotoxicity of Cholesterol Oxidase To Cells Of Hypercholesterolemic Guinea Pigs," *Comparative Biochemistry and Physiology*, vol. 94C, No. 1, 1989, pp. 105–110.

Albesa, "*Klebsiella pneumoniae* haemolysin adsorption to red blood cells," *Journal of Applied Bacteriology*, vol. 67, No. 3, Sep. 1989, pp. 263–266.

Hoogevest et al., "Effect of Amphotericin B on Cholesterol–Containing Liposomes of Egg Phosphatidylcholine and Didocosenoyl Phosphatidylcholine," *Biochimica Et Biophysica Acta*, vol. 511, No. 3, Aug. 17, 1978, pp. 397–407.

Seeger et al., "The Haemolytic Effect of Phallolysin," *Archives of Pharmacology*, vol. 293, No. 2, May 1976, pp. 163–170.

Hase et al., "The Structure–Hemolysis Relationship of Oleanolic Acid Derivatives and Inhibition of the Saponin–Induced Hemolysis with Sapogenins," *Journal of Pharmacobio–Dynamics*, vol. 4, No. 11, Nov. 1981, pp. 833–837.

Hatch et al., "The Use Of Cetavlon In A Diluent For Counting Leukocytes In The Coulter Electronic Counter," *The American Journal of Clinical Pathology*, vol. 36, No. 3, Sep. 1961, pp. 220–223.

Owellen et al., "Cytolytic Saponin Fraction From Asterias Vulgaris," *Toxicon*, vol. 11, No. 4 Jul. 1973, pp. 319–323.

Warren et al., "Cholesterol is excluded from the phospholipid annulus surrounding an active calcium transport protein," *Nature*, vol. 255, Jun. 26, 1975, pp. 684–687.

Badimon et al., "Platelet Deposition at High Shear Rates Is Enhanced by High Plasma Cholesterol Levels," *Arteriosclerosis and Thromboisis*, vol. 11, No. 2, Mar./Apr. 1991, pp. 395–402.

Esfahani et al., "Effects of cholesterol and lipoproteins on endocytosis by a monocyte–like cell line," *Biochimica et Biophysica Acta*, vol. 889, No. 3, Dec. 19, 1986, pp. 287–300.

Kirch et al., "The Relationship Of Membrane Lipids To Species Specific Hemolysis by Hemolytic Factors From *Stomoxys calcitrans* (L.) (Diptera: Muscidae)," *Insect Biochemistry*, vol. 21, No. 2, 1991, pp. 113–120.

Bomford, "Saponin and Other Haemolysins (Vitamin A, Aliphatic Amines, Polyene Antibiotics) as Adjuvants for SRBC in the Mouse," *International Archives of Allergy and Applied Immunology*, vol. 63, No. 2, 1980, pp. 170–177.

Bomford, "Studies on the Cellular Site of Action of the Adjuvant Activity of Saponin for Sheep Erythrocytes," *International Archives of Allergy and Applied Immunology*, vol. 67, Feb. 1982, pp. 127–131.

Cordera et al., "Insulin Receptor Binding On Red Cells Of Hypertriglyceridemic Patients," *Diabete & Metabolisme*, vol. 11, Jun. 1985, pp. 137–140.

Imai et al., "The Mechanism Of The Action Of Prymnesium Toxin On Membranes," *Biochimica et Biophysica Acta*, vol. 352, No. 3, Jun. 29, 1974, pp. 344–348.

Segelman et al., "Biological and Phytochemical Evaluation of Plants. False–Negative Saponin Test Results Induced by the Presence of Tannins," *Lloydia*, vol. 32, No. 1 Mar., 1969, pp. 52–58.

Assa et al., "Interaction of Alfalfa Saponins With Components Of The Erythrocyte Membrane In Hemolysis," *Biochimica et Biophysica Acta*, vol. 307, No. 1, Apr. 25, 1973, pp. 83–91.

Isomaa et al., "Shape transformations induced by amphiphiles in erythrocytes," *Biochimica et Biophysica Acta*, vol. 899, No. 1, May 12, 1987, pp. 93–103.

Segal et al., "The protective action of glycyrrhizin against saponin toxicity," *Biochemical pharmacology*, vol. 26, No. 7, Apr. 1, 1977, pp. 643–645.

Ding–E Young et al., "Dissociation Of Membrane Binding And Lytic Activities Of The Lymphocyte Pore–Forming Protein (Perforin)," *The Journal of Experimental Medicine*, vol. 165, No. 5, May 1, 1987, pp. 1371–1382.

Connor et al., "Maintenance of lipid asymmetry in red blood cells and ghosts: effect of divalent cations and serum albumin on the transbilayer distribution of phosphatidylserine," *Biochimica et Biophysica Acta*, vol. 1025, No. 1, Jun. 11, 1990, pp. 82–86.

Morimoto et al., "Interaction of Saposins, Acidic Lipids, and Glucosylceramidase," *The Journal of Biological Chemistry*, vol. 265, No. 4, Feb. 5, 1990, pp. 1933–1937.

James H. Jandl, M.D., Blood, Chapter 2 "Physiology of Red Cells," pp. 49–109.

Rai et al., "A Morphometric and X–ray Energy Dispersive Approach to Monitoring pH–Altered Cadmium Toxicity in *Anabaena flos–aquae*," *Archives of Environmental Contamination and Toxicology*, vol. 19, No. 4 Jul.–Aug. 1990, pp. 481–487.

Frade et al., "Hypofibrinolysis Associated With Vasculopathy In Non Insulin Dependent Diabetes Mellitus," *Thrombosis Research*, vol. 59, No. 1, Jul. 1, 1990, pp. 51–59.

Schwartz et al., "A phase I trial of recombinant tumor necrosis factor (rTNF) administered by continuous intravenous infusion in patients with disseminated malignancy," *Biotherapy*, vol. 1, No. 3, 1989, pp. 207–214.

Hornsby et al., "Hemostatic Alternations With Exercise Conditioning in NIDDM," *Diabetes Care*, vol. 13, No. 2, Feb. 1990, pp. 87–92.

McKinney, "Shark Cytotoxic Macrophages Interact with Target Membrane Amino Groups," *Cellular Immunology*, vol. 127, No. 2, May 1990, pp. 506–513.

Stewart et al., "Dependence of the Surface Expression of the Glycolipid Cerebroside Sulfate on Its Lipid Environment: Comparison of Sphingomyelin and Phosphatidylcholine," *Biochemistry*, vol. 29, No. 15, Apr. 17, 1990, pp. 3644–3653.

Liu et al., "Interactions of Serum Proteins with Small Unilamellar Liposomes Composed of Dioleoylphosphatidylethanolamine and Oleic Acid: High–Density Lipoprotein, Apolipoprotein A1, and Amphipathic Peptides Stabilize Liposomes," *Biochemistry*, vol. 29, No. 15, Apr. 17, 1990, pp. 3637–3643.

Seilan et al., "Effects of Oxysterols on Arachidonic Acid Metabolism and Prostacyclin Synthesis in Bovine Aortic Smooth Muscle Cells in Culture," *Prostaglandins Leukotrienes And Essential Fatty Acids*, vol. 39, No. 1, Jan. 1990, pp. 11–18.

Kubotsu et al., "Colorimetric Liposome Lysis for Assay of Anti–Streptolysin O Antibody," *Clinical Chemistry*, vol. 10, 1990, pp. 1747–1749.

Fukuda et al., "Incomplete synthesis of N–glycans in congenital dyserythropoietic anemia type II caused by a defect in the gene encoding α–mannosidase II," *Proceedings of the National Academy of Sciences*, vol. 87, No. 19, Oct. 1990, pp. 7443–7447.

Iwamoto et al., "Effect of isolated C–terminal fragment of 0–toxin (perfringolysin O) on toxin assembly and membrane lysis," *European Journal of Biochemistry*, vol. 194, No. 1, Nov. 1990, pp. 25–31.

Ding–E Young et al., "Channel Fluctuations Induced By Membrane Attack Complex C53–9," *Molecular Immunology*, vol. 27, No. 10, Oct. 1990, pp. 1001–1007.

Nagai et al., "Role of Pancreatic Enzymes and Their Substrates in Autodigestion of the Pancreas," *Gastroenterology*, vol. 96, No. 3 Mar. 1989, pp. 838–847.

Janowitz et al., "Medikamentöse Cholelitholyse und Nukleationszeit," *DMW*, Jun. 23, 1989, pp. 983–985.

Ellens et al., "Membrane Fusion and Inverted Phases," *Biochemistry*, vol. 28, No. 9, May 2, 1989, pp. 3692–3703.

Hellstern et al., "Perkutan–transhepatische Lyse von Gallenblasensteinen mit Methyl–tert–butyl–äther," *DMW*, Mar. 31, 1988, pp. 506–510.

Miyake et al., "Purification and Characterization of *Vibrio metschnikovii* Cytolysin," *Infection and Immunity*, vol. 56, No. 4, Apr. 1988, pp. 954–960.

Shasby, et al., "Exogenous Oxidans Initiate Hydrolysis of Endothelial Cell Inositol Phospholipids," *Blood*, vol. 72, No. 2, Aug. 1988, pp. 491–499.

Post et al., "Phospholipid asymmetry in cardiac sarcolemma. Analysis of intact cells and 'gas–dissected' membranes," *Biochimica et Biophysica Acta*, vol. 943, No. 1, Aug. 4, 1988, pp. 256–266.

Chong et al., "Blocking Of Lymphokine Activated Killer (LAK) Cell Mediated Cytotoxicity By Cell–Sized Beads Bearing Tumor Cell Proteins," *The Journal of Immunology*, vol. 141, No. 12 Dec. 15, 1988, pp. 4418–4424.

Tachibana et al., "In Vitro Lysis of the Bloodstream Forms of *Trypanosoma brucei gambiense* by Stearylamine–Bearing Liposomes," *Antimicrobial Agents and Chemotherapy*, vol. 21, No. 7, Jul. 1988, pp. 966–970.

Bourre, "Radicaux libres, acides gras polyinsaturés, mort cellulaire, vieillissement cerebral," *Société De Biologie*, vol. 182, 1988, pp. 5–36.

Petry et al., "Sulfated lipids represent common antigens on the surface of *Trypanosoma cruzi* and mammalian tissues," *Molecular and Biochemical Parasitology*, vol. 30, 2, Aug. 1988, pp. 113–122.

Fernández–Zamorano et al., "Hemolytic Anemia And Susceptibility To Hydrogen–Peroxide Hemolysis In Children With Vitamin E—Deficiency And Chronic Liver Diseae," *Journal of Medicine*, vol. 19, Nos. 5 & 6, 1988, pp. 317–334.

Caleffi et al., "Effect of tamoxifen on oestrogen binding, lipid and lipoprotein concentrations and blood clotting parameters in premenopausal women with breast pain," *Journal of Endocrinoloyg*, vol. 119, No. 2, Nov. 1988, pp. 335–339.

Avellone et al., "Changes Induced By Gemfibrozil On Lipidic, Coagulative And Fibrinolytic Pattern In Patients With Type IV Hyperlipoproteinemia," *International Angiology*, vol. 7, No. 3, Jul.–Sep. 1988, pp. 270–277.

Weinstein et al., "Kinetics Of Hemolysis Induced By A Toxin From *Bacillus thuringienisis israelensis*," *Toxicon*, vol. 26, No. 12, 1988, pp. 1177–1185.

Thakur et al., "The Ayurvedic medicines Haritaki, Amla and Bahira reduce cholesterol–induced atherosclerosis in rabbits," *International Journay of Cardiology*, vol. 21, No. 2, Nov. 1988, pp. 167–175.

Richards et al., "Membrane proteins are critical targets in free radical mediated cytolysis," *Biochimica et Biophysica Acta*, vol. 946, No. 2, Dec. 22, 1988, pp. 281–288.

Rafter et al., "Cellular toxicity of fecal water depends on diet," *The American Journal Clinical Nutrition*, vol. 45, No. 3, Mar. 1987, pp. 559–563.

Juliano et al., "Mechanism of the Selective Toxicity of Amphotericin B Incorporated Into Liposomes," *Molecular Pharmacology*, vol. 31, No. 1, Jan. 1987, pp. 1–11.

Rilfors et al., "Lipid Acyl Chain–Dependent Effects of Sterols in *Acholeplasma laidlawii* Membranes," *Journal of Bacteriology*, vol. 169, No. 2, Feb. 1987, pp. 830–838.

Geoffroy et al., "Purification, Characterization, and Toxicity of the Sulfhydryl–Activated Hemolysin Listeriolysin O from *Listeria monocytogenes*," *Infection and Immunity*, vol. 55, No. 7, Jul. 1987, pp. 1641–1646.

Tomita et al., "The Action of Sphingomyelinase from *Bacillus cereus* on ATP–Depleted Bovine Erythrocyte Membranes and Different Lipid Composition of Liposomes," *Archives of Biochemistry and Biophysics*, vol. 255, No. 1, May 15, 1987, pp. 127–135.

Isomaa et al., "Shape transformations induced by amphiphiles in erythrocytes," *Biochimica et Biophysica Acta*, vol. 899, No. 1, May 12, 1987, pp. 93–103.

Shirazi et al., "Release of Leukotriene $B_4$ from Sublethally Injured Oligodendrocytes by Terminal Complement Complexes," *Journal of Neurochemistry*, vol. 48, No. 1, Jan. 1987, pp. 271–278.

Hauser, "Spontaneous Vesiculation of Uncharged Phospholipid Dispersions Consisting of Lecithin and Lysolecithin," *Chemistry and Physics of Lipids*, vol. 43, No. 4, May 1987, pp. 283–299.

Tellier et al., "Interactions between biliary lipid micelles and intestinal brush border membranes investigated by $^1$H and $^{31}$P nuclear magnetic resonance," *European Biophysics Journal*, vol. 15, No. 3, Dec. 1987, pp. 177–184.

Bernheimer et al., "Some Properties Of Flammutoxin From the Edible Mushroom *Flammulina velutipes*," *Toxicon*, vol. 25, No. 11, 1987, pp. 1145–1152.

Crook et al., "Characterization Of Anti–Cerebroside Sulfate Antisera Using A Theoretical Model To Analyse Liposome Immune Lysis Data," *Molecular Immunology*, vol. 24, No. 11, Oct. 1987, pp. 1135–1143.

Greiner et al., "Biliäre Stoßwellen–Lithotripsie," *DMW*, vol. 49, Dec. 4, 1987, pp. 1893–1896.

Thormar et al., "Inactivation of Enveloped Viruses and Killing of Cells by Fatty Acids and Monoglycerides," *Antimicrobial Agents and Chemotherapy*, vol. 31, No. 1, Jan. 1987, pp. 27–31.

Lawaczeck et al., "Interaction of negatively charged liposomes with nuclear membranes: adsorption, lipid mixing and lysis of the vesicles," *Biochimica et Biophysica Acta*, vol. 903, No. 1, Sep. 18, 1987, pp. 123–131.

Singh et al., "Interrelationship Between Hemolysis and Lipid Peroxidation of Human Erythrocytes Induced by Silicic Acid and Silicate Dusts," *Journal of Applied Toxicology*, vol. 7, No. 2, Apr. 1987, pp. 91–96.

Girotti et al., "Lipid Peroxidation in Erythrocyte Membranes: Cholesterol Product Analysis in Photosensitized and Xanthine Oxidase–Catalyzed Reactions," *Lipids*, vol. 22, No. 6, Jun. 1987, pp. 401–408.

Ichikawa et al., "Lipid Peroxidation Is Not the Cause of Lysis of Human Erythrocytes Exposed to Inorganic or Methylmercury," *Archives of Biochemistry and Biophysics*, vol. 259, No. 1, Nov. 15, 1987, pp. 46–51.

Watarai et al., "Application of Liposomes to Generation of Monoclonal Antibody to Glycosphingolipid: Production of Monoclonal Antibody to GgOse$_4$Cer," *The Journal of Biochemistry*, vol. 102, No. 1, Jul. 1987, pp. 59–67.

Yue et al., "Inhibition Of Cytolysin Activity In Large Granular Lymphocyte Granules By Lipids: Evidence For A Membrane Insertion Mechanism Of Lysis," *Molecular Immunology*, vol. 24, No. 6, Jun. 1987, pp. 647–653.

Jeannin et al., "Correlation Between the Synergistic Effect of Liposomes and Endotoxins on the Activation of Macrophage Tumoricidal Activity and the Effect of Liposomes on the Rough Endoplasmic Reticulum of Macrophages," *The Journal of Membrane Biology*, vol. 104, No. 2, Sep. 1988, pp. 107–118.

Eriksson, "Spontaneous association of purified major histocompatibility class I antigens with recipient cells after removal of detergent," *Journal of Immunological Methods*, vol. 115, No. 1, 1988, pp. 133–139.

Bertoni et al., "Xanthoma of Bone," *American Journal of Clinical Pahtology*, vol. 90, No. 4, Oct. 1988, pp. 377–384.

Andersen et al., "Increased Fibrinolytic Potential after Diet Interventions in Health Coronary High–risk Individuals," *Acta Medica Scandinavica*, vol. 223, No. 6, 1988, pp. 499–506.

Vazquez–Boland et al., "Preliminary evidence that different domians are involved in cytolytic activity and receptor (cholesterol) binding in listeriolysin O, the *Listeria monocytogenes* thiol–activated toxin," *FEMS Microbiology Letters*, Nov. 1989, pp. 95–100.

Knowles et al., "Activation of insect cell adenylate cyclase by *Bacillus thuringiensis* δ–endotoxins and melittin," *The Biochemical Journal*, vol. 253, No. 1, Jul. 1, 1988, pp. 235–241.

MacDonald, "Phosphatidylserine Vesicle Lysis by Sendai Virus at Low pH Is Not Due to Virus–Vesicle Fusion," *Archives of Biochemistry and Biophysics*, vol. 265, No. 1, Aug. 15, 1988, pp. 62–72.

Skarlatos et al., "Biochemical Characterization of Isolated Cholesterol–Phospholipid Particles Continuously Released from Rat and Human Platelets After Activation," *Laboratory Investigation*, vol. 59, No. 3, Sep. 1988, pp. 344–352.

Sitaramam et al., "Hydrogen peroxide permeation across liposomal membranes: a novel method to assess structural flaws in liposomes," *Molecular and Celluarl Biochemistry*, vol. 91, Nos. 1/2, Nov./Dec. 19, 1989, pp. 91–97.

Manabe et al., "Effect of Host Lattice on Antigenicity of Glycophorin in Membranes," *Chemical & Pharmaceutical Bulletin*, vol. 37, No. 10, Oct. 1989, pp. 2757–2761.

Rozycka et al., "Dynamika zmian mieśnia sercowego w hipercholesterolemii doświadczalnej," *Polski Tygodnik Lekarski*, vol. 44, Apr. 10, 1989, pp. 247–252.

Besson et al., "Action of mycosubtilin on erythrocytes and artificial membranes," *Microbios*, vol. 59, 1989, pp. 137–143.

Masaki et al., "Assay of complement activity in human serum using large unilamellar liposomes," *Journal of Immunological Methods*, vol. 123, No. 1, 1989, pp. 19–24.

Carson et al., "Plasminogen Activator Inhibitor in Plasma Is Related to Testosterone in Men," *Metabolism*, vol. 38, No. 10, Oct. 1989, pp. 1010–1015.

Künnert, "Cholesterol metabolism in arteriosclerotic intima," *Zentralblatt Für Allgemeine Pathologie Und Pathologische Anatomie*, vol. 135, No. 6, 1989, pp. 505–509.

Mancini et al., $\alpha_{2u}$–Globulin in Modified Sebaceous Glands with Pheromonal Functions: Localization of the Protein and Its mRNA in Preputial, Meibomain, and Perianal Glands, *The Journal of Histochemistry and Cytochemistry*, vol. 37, No. 2, Feb. 1989, pp. 149–157.

Kurtz et al., "Orale und direkte Lyse von Gallenblasensteinen," *Fortschritte der Medizin*, vol. 20, Jul. 10, 1989, pp. 443–445.

Shiao et al., "The solubilization and morphological change of human platelets in various detergents," *Biochimica et Biophysica Acta*, vol. 980, No. 1, Mar. 27, 1989, pp. 56–68.

Roozemond et al., "Liposomes Can Function As Targets For Natural Killer Cytotoxic Factor But Not For Tumor Necrosis Factor," *The Journal of Immunology*, vol. 142, No. 4, Feb. 15, 1989, pp. 1209–1216.

Burt et al., "Calcium Pyrophosphate and Monosodium Urate Crystal Interactions with Neutrophils: Effect of Crystal Size and Lipoprotein Binding to Crystals," *The Journal of Rheumatology*, vol. 16, No. 6, Jun. 1989, pp. 809–817.

Furlong et al., "*Schistosoma mansoni*: Synthesis and Rlease of Phospholipids, Lysophospholipids, and Neutral Lipids by Schistosomula," *Experimental Parasitology*, vol. 69, No. 1, Jul. 1989, pp. 65–77.

El Hajji et al., "Interaction of trichorzianines A and B with model membranes and with the amoeba Dictyostelium," *Biochimica et Biophysica Acta*, vol. 978, No. 1, Jan. 16, 1989, pp. 97–104.

Daemen et al., "Conditions controlling tumor cytotoxicity of rat liver macrophages mediated by liposomal muramyl dipeptide," *Biochimia et Biophysica Acta*, vol. 991, No. 1, Apr. 25, 1989, pp. 145–151.

Needham et al., "Electro–mechanical permeabilization of lipid vesicles," *Biophysical Journal*, vol. 55, No. 5, May 1989, pp. 1001–1009.

Hajduk et al., "Lysis of *Trypanosoma brucei* by a Toxic Subspecies of Human High Density Lipoprotein," *The Journal of Biological Chemistry*, vol. 264, No. 9, Mar. 25, 1989, pp. 5210–5217.

Chandra, "Hepatic Mitochondrial Membranolysis Repairing by Spermidine," *Vitamin and Nutrition Research*, vol. 59, No. 2, 1989, pp. 113–116.

Alouf et al., "Interaction of staphylococcal δ–toxin and synthetic analogues with erythrocytes and phospholipid vesicles," *European Journal of Biochemistry*, vol. 183, No. 1, Aug. 1989, pp. 381–390.

Gauduel et al., "Enzyme Release and Mitochondrial Activity in Reoxygenated Cardiac Muscle: Relationship with Oxygen–Induced Lipid Peroxidation," *General Physiology and Biophysics*, vol. 8, No. 4, Aug. 1989, pp. 327–340.

Glauert et al., "Action of Saponin on Biological Cell Membranes," *Nature*, vol. 196, No. 4858, Dec. 8, 1962, pp. 952–955.

Bader et al., "Theory of Coincidence Counts and Simple Practical Methods of Coincidence Count Correction for Optical and Resistive Pulse Particle Counters," Rev. Sci. Instrum. 43(10):1407–1412 (1972).

Bagwell et al., "A Simple and Rapid Method for Determining the Linearity of a Flow Cytometer Amplification System," Cytometry 10:689–694 (1989).

Coulter STKS Operator's Guide (1992).

Cowan et al., "The Linearity and Response of Focused Apertures," Part. Part. Syst. Charact. 7:1–5 (1990).

Cowan et al., "The linearity and response of focused apertures," Chem. Abstr. 112(24):219757s (1990).

Durand, "Calibration of Flow Cytometer Detector Systems," Methods Cell Biol. 42:597–604 (1994).

Eisert, "Cell Differentiation Based on Absorption and Scattering," J. Hostochem. Cytochem. 27(1):404–409 (1979).

Figueiredo et al., "Mass Calibration of the Coulter Counter Model ZM," Part. Part. Syst. Charact. 8:294–296 (1991).

Figueiredo et al., "Mass calibration of the Coulter Counter model ZM," Chem. Abstr. 117(14):133396q (1992).

Figueiredo et al., "Testing mass calibration with the Coulter counter," Chem. Abstr. 118(12):105383k (1993).

Gilmer et al., Calibration methods for automated hematology instruments, Chem. Abstr. 87(15):114045v (1977).

Inaoka et al., "Evaluation of the New Vials of NE CHECK Control Blood for the NE Series, an Automated Hematology Analyzer," Sysmex J. 15(3):241–248 (1992).

Information Sheet—Unipath Cell–Dyn Opti–Cal.

Introduction to SE CHECK, a Newly–developed Control Blood for the Sysmex SE–9000 Automated Hematology Analyzer Hematology Analyzer, Sysmex J. Int. 4:36–42.

Kairisto et al., Quality Control; of Multichannel Hematology Analyzers, Bivariate On–line Comparison of MCV and MCH Values for the Detection of Random Errors, Am. J. Clin. Pathol. 97:645–651 (1992).

Lindmo et al., "Flow Cytometric measurement of the Polarization of Fluorescence from Intracellular Fluorescein in Mammalian Cells," Biophys. J. 18:173–187 (1977).

Mulry, "Hematology instrumentation to improve laboratory productivity," Amer. Clin. Lab. 14(2):12–13 (Feb. 1995).

Nelley et al., "Automated Simultaneous Leukycyte Counting and Hemoglobin Determinations Using the Coulter Counter and the AutoAnalyzer," Amer. J. Clin. Pathol. 56:493–499 (1971).

Parks et al., "Automatic Standardization, Compensation Adjustment and Instrument Diagnosis System for Flow Cytometers," Soc. Analytical Cytology, Supp. 4, p. 70, abstract 433B (1990).

Robinson et al., "Technique for Cellular Fluorescence Distribution Analysis," Cytometry 10:402–409 (1989).

Shapiro et al., "Combined Blood Cell Counting and Classification with Fluorochrome Stains and Flow Instrumentation," J. Histochem. Cytochem. 24(1):396–411 (1976).

Sikdar et al., "Evaluation and Calibration of the Model T Coulter Counter Used in the Population Mode," Anal. Chem. 48(9):1415–1418 (1976).

Vogt et al., "Model System Evaluating Fluorescein–Labeled Microbeads as Internal Standards to Calibrate Fluorescence Intensity on Flow Cytometers[1,2]," Cytometry 10:294–302 (1989).

* cited by examiner

HEMATOLOGICAL REFERENCE CONTROL COMPOSITION CONTAINING LEUKOCYTE ANALOGS, METHODS OF MAKING, AND USES THEREOF

CROSS REFERENCE TO RELATED APPLICATION

This is a continuation of application Ser. No. 08/787,408, filed Jan. 22, 1997; which is a continuation of Ser. No. 08/432,435 filed Apr. 28, 1995, now abandoned; which is a continuation-in-part of Ser. No. 08/386,711 filed Feb. 8, 1995, now U.S. Pat. No. 5,529,933; which is a continuation of Ser. No. 08/081,529 filed Jun. 23, 1993, now abandoned; which is a continuation of Ser. No. 07/840,438 filed Feb. 24, 1992, now abandoned all of which are incorporated herein by reference.

FIELD OF INVENTION

This invention relates to a novel method to increase the system quality control capabilities of hematology instruments. The method has particular utility for instruments which measure (1) volume measured by D.C. current, (2) high frequency (RF) size, (3) opacity, and (4) light scatter to discriminate cell populations of blood. The method has found additional utility for instruments which measure (1) volume measured by D.C. current and (2) high frequency (RF) size. The method has also found utility for instruments that measure cell volume only by D.C. current.

BACKGROUND OF THE INVENTION

Quality control long has been a necessary and routine procedure in clinical hematology. Accuracy in the counting of red blood cells and white blood cells, including differentiating among the subpopulations of white blood cells is dependent, in part, upon the use of adequate control products and methods of using the control products. With the numerous types of equipment for particle counting now available, quality control by the use of control products is necessary, since the possibility of malfunctioning of the instrument is ever present. The traditional method of maintaining a quality control program for automatic particle counting equipment has consisted of providing fresh human blood as a whole blood standard. However, this fresh blood is usable for only one day, therefore, durable blood products were developed.

Hematology control products, which contain reference blood cell analogs, which monitor the accuracy and precision of blood cell counting devices are important. It is recognized that there is a present need for new methods of using blood cell analogs for maintaining the accuracy of white cell differentiation and other parameters when employing such blood cell counting devices.

The control products should approximate that of fresh whole blood as closely as possible. Attempts have been made to provide suitably sized particles in stable suspensions by the use of ragweed pollen, polystyrene, latex, various organic materials and fixed human red cells. None of these suspensions have proved suitable for use as a control product for white cell differentiation of at least four sub-populations of leukocytes.

The material used for maintaining quality control, hereinafter called a hematology control product or control product, can under specific circumstances be used also to calibrate hematology instruments. For the purposes of this invention, the control product used in the method to determine whether an instrument is properly functioning will contain one or more analogs suspended in a liquid media, which when analyzed simulates at least one physical or biological property of blood which the instrument is capable of analyzing. As used herein, an analog is defined as a particle which simulates at least one physical or biological property of a target population. As such, some automatic machines are able to analyze only certain components of a control product, despite the control product having additional parameter components susceptible to analysis by other machines. Heretofore, there has been an absence of methods developed for using a control product to provide quality control of the instrument's performance. Control products typically provide checks for at least four subgroups of leukocytes namely, lymphocytes, monocytes, neutrophils and eosinophils. Prior art use of control products have focused upon checking whether the instrument provides the proper count and percentage of the analogs. However, the method of this invention provides additional information to evaluate and diagnose instrument performance.

It is evident that a control product must accurately indicate, on a comparative basis, what a test sample of fresh blood constitutes with regard to the determinations in question. It is further evident how important it is for the control product to simulate fresh blood, since blood components, such as red blood cells, can hemolyze slowly and undergo changes in size and shape within hours after removal from a blood donor. Similarly, non stabilized white blood cells suffer degenerative changes.

In general, the process of the prior art for making analogs focused on using red blood cells which had maintained or reduced their original volume prior to fixation. Shrinking or expansion of the cells by manipulating their osmotic environment prior to fixation has had its limitations. Previously, shrinking or swelling non-human erythrocytes more than about 30% to 50% caused excessive cell association or lysis of the cell.

U.S. Pat. No. 3,873,467 to Hunt teaches a hematologic reference control comprising a suspension of washed, stabilized human red blood cells in a nonproteinaceous aqueous suspension fluid that replaces the plasma in human blood. Stability in the reference control is attained by conditioning the cells by the inclusion in the aqueous suspension fluid of materials tending to make the cells assume a spherical shape, without substantial change in the mean cell volume of the cells, as well as imparting to the cells a resistance to the normal tendency of degrading with time. The aqueous suspension fluid furthermore produces an environment for the cells inhibiting biological activity. In a preferred embodiment there is further included in the reference control a minor amount of fixed human red blood cells, processed to have a substantially increased mean cell volume. The fixed cells are resistant to a change in cell volume, and to dissolution under the action of lysing reagents producing lysing of the stabilized cells. The fixed red blood cells in the reference control substitute for the white cell population in human blood.

In U.S. Pat. No. 4,704,364, to Carver, et al., there are disclosed controls for thresholds and additional operational performances for electronic particle counters typified by the COULTER COUNTER® Model S-Plus type analyzers. However, there is now a need for new methods of using a whole blood cell control product for electronic optical particle counters typified by the COULTER® VCS analyzer. The VCS analyzer permits the differentiation of at least four populations of leukocytes.

Any system for automated differential counting of human leukocytes, which distinguishes at least four populations of leukocytes from other cells in the blood on the basis of size range, volume distribution, light scatter range, and electrical opacity and conductivity sensitivities requires that the control product closely simulate the range, distribution and sensitivities characteristics of the respective cells in normal human blood.

Human lymphocytes, monocytes, neutrophils, basophils and eosinophils have a specific size distribution range and optical characteristics. Both the upper and lower size limits for each subpopulation of leukocytes should be represented in a reference control product. In addition, the mean cell volume of each leukocyte subpopulation in the control product should approximate that of normal human blood. Moreover, it is necessary that the liquid suspension media used for the control product does not cause significant shrinking or swelling of the cells. Still further, the aging of the control product should not result in deterioration of the volume distribution histogram characteristics or other parameters. A further requirement for the leukocyte analogs in the control product for multi-parameter instruments is that in order to be counted and differentiated, the analog cells in a whole blood control product must not be completely lysed by the lytic reagent.

A variety of media have been used in conjunction with blood cell analogs. In U.S. Pat. No. 4,299,726, a multi-purpose diluent and a media is disclosed. The diluent is used to precondition red blood cells and consists essentially of lactose, sodium azide and a non-ionic surfactant; is pH adjusted and osmolality adjusted. The media is used for a carrier of the whole blood control product and includes lactose, fungicides and antibiotics. It also includes additional components which alter red blood cell membranes, including bile salts and cholic acid derivatives, phenothiazine compounds and the salts thereof having antihistamine properties, and 4-amino-benzoic acid ester derivatives and their salts having local anesthetic properties.

One disadvantage of the prior art medias is that, when used in conjunction with red blood cells and fixed human white blood cells or white blood cell analogs, the control product does not simulate a whole blood sample in instruments which differentiate at least four subpopulations of leukocytes. The specific parameters of the red and white blood cells which it is desirable to measure dictate some of the necessary characteristics of a suitable media for a whole blood reference control product. It is desirable to know the volume of the red cell. Once this measurement is ascertained and the red cells have been counted, the packed cell volume or hematocrit can be computed. Therefore, the suspension media of the control product should be capable of equilibrating and stabilizing the volume of red blood cells in the sample so that its mean cell volume can be measured (MCV).

A control product should also be rendered free of any particulate matter that would perhaps demonstrate interference in lower size thresholds corresponding to that of human platelet size and distribution. Concomitantly, the suspension media would optionally include bacteriostatic agents to prevent the growth of microorganisms after packaging the control product.

Although red blood cells (erythrocytes) and white blood cells (leukocytes) nominally have different sizes, their size ranges tend to overlap, or at least under certain conditions of health could overlap. Moreover, the opacity of these two types of blood cells also may overlap. Erythrocytes and the lymphoid leukocytes unfortunately overlap considerably in cell sizes, and it is not practical to count one in the presence of the other by size discrimination alone. Traditional practice involved the use of a strong lytic reagent that stromatolyses the erythrocytes, reducing them to very small particles or causing membrane solubilization, to eliminate them from being counted; and strips most, if not all, of the cytoplasm from the leukocytes, leaving only their lyse-resistant nuclei to be counted. Since original leukocyte cell volume is drastically affected and reduced to a minimum, only a single leukocyte population is discernible by this older form of blood cell size analysis.

U.S. Pat. No. 3,741,875, Ansley et al., describes, a process for obtaining a differential white blood cell count. A cytological fixing agent, which is a monoaldehyde, such as formaldehyde, is added to a blood sample. A hemolyzing agent is added after the fixation step to cause the red blood cells to release their hemoglobin content into solution. Addition of a specific cytochemical substrate, chromogenic precipitating coupling reagent, and pH buffer causes deposition of an insoluble dye in a specific type of cell containing an immobilized enzyme. The solution containing the dyed blood cells then is passed through a photometric counter. Using different specific substrates for different enzymes contained in specific kinds of cells, absolute and relative counts of the different kinds of cells are obtained. The cytological fixing solution utilized only a monoaldehyde. Dialdehydes are stated to be unsuitable, since they cross-link and produce extracellular precipitates.

U.S. Pat. No. 4,485,175, to Ledis, et al., concerns a method and reagent system for three-volume differential determination of lymphocyte, mononuclear, and granulocyte populations of leukocytes, using quaternary ammonium salts as lysing agents and the COULTER COUNTER® Model S-Plus automated blood counter, which instrument employs only direct current field excitation.

U.S. Pat. No. 4,751,179 to Ledis, et al. describes a reagent system, including saponin in a lysing reagent and a rapidly active cross-linking agent such as glutaraldehyde as a fixing reagent, which reproducibly affects whole blood to cause the red blood cells to stromatolyze and modifies the leukocytes to generate data to define four distinct clusters for detection and classification by flow analysis instrumentation. The clusters represent the four major leukocyte types found in blood: lymphocytes, monocytes, neutrophils and eosinophils, thus providing a method of leukocyte differential analysis. According to Ledis, et al., previous methods of flow analysis of leukocytes using D.C. volume, or light scatter at various angles have shown only three clusters of leukocytes, corresponding to lymphocytes, granulocytes and monocytes. The parameters used by Ledis, et al. for the leukocyte classification include combinations of two or more of DC (Coulter) volume, high frequency (RF) size, Coulter opacity (RF size/DC volume), light scatter at various angular ranges, and fluorescence at various wavelengths of illumination.

Electronic counters which employ the Coulter Principle, first described in U.S. Pat. No. 2,656,508, express a true reflection of particle counts. According to the Coulter Principle, when a particle of microscopic size is suspended in an electrolyte liquid, is passed through an electrical field of small dimensions of an order approaching those of a particle, there will be a momentary change in the field's electric impedance. If the electrical field is excited by a direct (DC) or low frequency current, the electrical change is closely proportional to the volume of the particle. In commercial apparatus, the changes are detected by some suitable means and used to operate counters and analyzers. The analyzers associated with such apparatus classify and size particles into populations based upon particle volume and record the data obtained.

The Coulter Principle invention was expanded materially in U.S. Pat. No. 3,502,974, Coulter, et al., using radio frequency (RF) current in addition to DC current field excitation, to provide not only DC volume information concerning the particle studied, but also information due to the composition and nature of the material constituting the particle. This patent discloses apparatus capable of distinguishing between particles of identical size, but of different material. By generating the particle sensing field by means of both a low frequency or direct current (DC) and radio frequency (RF) current excitation, two or more interrelated output signals can be derived from the passage of a single particle through the electrical field. This is due to the fact that, although the particles, such as blood cells, are nearly always insulators with respect to low frequency or direct current fields, they are capable of carrying or impeding radio frequency current differently from the surrounding electrolyte. This may be due to differences in the dielectric constant in the case of homogeneous particles, or to the sac-like structure in the case of blood cells which have, enclosed in an extremely thin membrane, contents having conductivities different from the electrolyte. Thus, while all the DC current goes around a blood cell, some of the RF current will go through it. The ease with which RF current will go through a particle is a measure of what is termed its "electrical transparency", or simply "transparency", in analogy with light transmission; whereas, a particle's ability to impede RF current is termed its "opacity". In later publications, "opacity" is defined as the RF impedance divided by the DC impedance.

The relative electrical opacity of a particle becomes an identifying feature of the particle contents and hence its particle type for classification purposes. To the extent that different types of particles each possess a different opacity, the difference between them is detectable. However, significantly different particles can possess substantially the same opacity and such particles cannot be classified effectively in this manner. In U.S. Pat. No. 3,836,849, Coulter, et al. taught that it is possible to change selectively the opacity of particle types by treatment of the particles, so that detectable differences result.

The COULTER COUNTER® Model S-Plus automated blood cell counter is designed to dilute a sample of whole blood in an isotonic diluent, add a lysing agent, and shortly thereafter begin counting. Thus, a diluent-lysing system must provide erythrocyte lysing kinetics sufficiently rapid to effect complete stromatolysation of the red blood cells (erythrocytes) during the lysing period. In addition, changes in leukocyte volume must be minimal during the data collection step, and ideally should be stable for several minutes.

COULTER Model VCS is a semi-automated analytical instrument that analyzes blood by using DC (Coulter) volume, Coulter opacity and light scatter at various angular ranges. The COULTER Model VCS uses a reagent system to obtain a five part differentiation in the total leukocyte count which provide quantitative analysis of the lymphocyte, monocyte, neutrophil, eosinophil and basophil population. The reagent system includes a quench, added after the weak "acid" lyse, the operation of which is to greatly reduce lytic action on the white cells. Shortly after the quench, the instrument begins measuring the volume, opacity and light scattering characteristics of the remaining white blood cells. The Model VCS must provide erythrocyte lysing kinetics sufficiently rapid to effect complete stromatolysation of the red blood cells during the lysing period while not affecting the leukocyte cells as to their volume, Coulter opacity and light scattering properties. The COULTER COUNTERS® instruments, with which this invention can be used, are the VCS, STKS and MAXM. However, the Model S and S-Plus types are not able to differentiate all of the subpopulations of leukocyte analogs which are in a whole blood control product, but rather can provide a total count of the leukocyte analogs. Certain of the S-Plus types are further able to differentiate two leukocyte subpopulations.

New electronic optical particle counting devices have made it necessary to develop new methods to determine whether an instrument is properly functioning within manufacturer's specification and diagnosing the cause of an instrument malfunction. Although this Specification will be directed primarily to method of using hematology control product useful with particle counters of the COULTER® type, it should be understood that the suspension media, analogs and control products disclosed herein, and their methods of use described herein, find wide application with particle counters generally. Accordingly, the term "electronic optical particle counter" should be understood to include, in addition to COULTER COUNTER® instruments, any other type of particle counter which discriminates between particles of various sizes by the use of electronic discriminator circuits ("thresholds") which respond electronically to signals indicative of particle size, mass, volume, opacity or light scatter. COULTER and COULTER COUNTER are Registered Trademarks of Coulter Corporation.

SUMMARY OF INVENTION

This invention relates to a method for using a hematology control product comprising placing a hematology control product in an instrument, said control product containing at least one leukocyte analog which has been derived from a blood cell which has been treated so that it is resistant to degradation by the lytic reagents used in the hematological test procedures, and the analog remains responsive to the reagents used in the performance of the instrument. The spatial position of the control product is analyzed from at least one member selected form the group comprising D.C. volume, RF size, opacity, and light scatter using new control parameters. More preferably, at least two different physical properties are measured. The results of such measurement are then reported to diagnose the cause of a malfunction of an instrument.

The invention further relates to a method of using a control product which contains at least one leukocyte analog population to determine if the instrument is functioning within manufacturer's analytical specifications. The method comprises placing a hematology control product in an instrument, said control product containing at least one leukocyte analog which has been derived from a blood cell which has been treated so that it is resistant to degradation by the lytic reagents used in the hematological test procedures, and the analog remains responsive to the performance of the instrument. The control product simulates at least one physical property of a human leukocyte, said property selected from the group comprising volume measured by D.C. current, high frequency (RF) size, opacity, and light scatter. More preferably, the control product simulates at least two physical properties of a human leukocyte. Then at least one, preferably two of the spatial positions from physical properties of the control product are measured. The results of such measurement are reported to diagnose the cause of a malfunction of an instrument.

Still further, the invention relates to a method comprising analyzing the spatial position of a leukocyte subpopulation in a quantity of patient blood samples to obtain a statistically significant value of a measured parameter, said analysis selected from at least one member of the group comprising D.C. volume, RF size, opacity, and light scatter; and reporting the results of such measurement in an instrument to diagnose the cause of a malfunction of an instrument.

Moreover, this invention also relates to combining a hematological sample with a cell suspension media comprising an aqueous solution of a plasma substance; and analyzing the resulting mixture in an instrument to diagnose the cause of an instrument malfunction, said analysis selected from at least one member and more preferably at least two members of the group comprising D.C. volume, RF size, opacity, and light scatter.

DETAILED DESCRIPTION OF THE INVENTION

Figure 1:
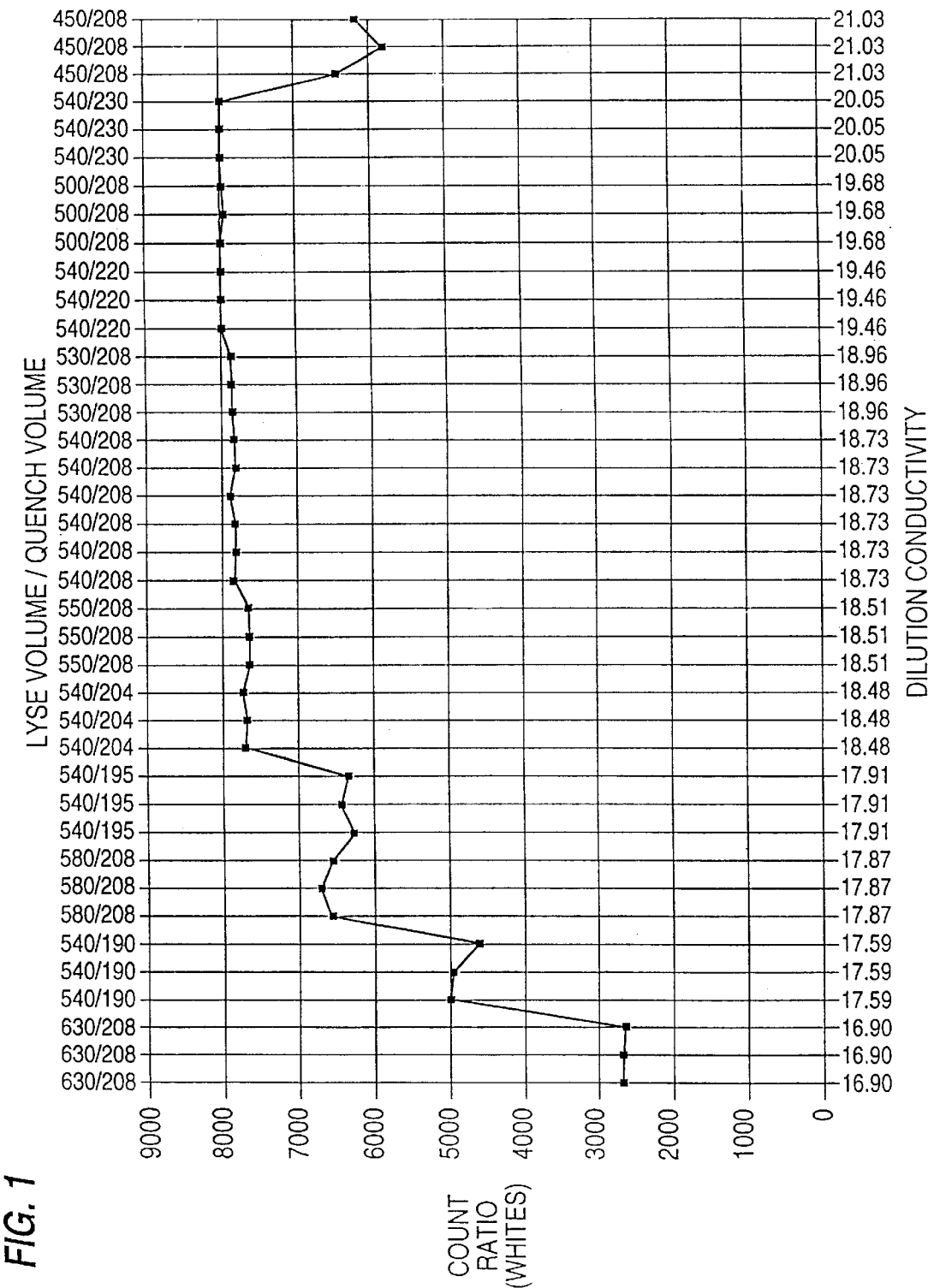
FIG. 1 is a comparison of the COUNT RATIO of the white blood cells compared to the conductivity of the diluted blood sample in the core that is to be tested.

For the purposes of understanding and explaining this invention, the following terms are defined.

Beads: Beads are particles (made, usually, of latex or some form of polystyrene) that can be used as stable and inert standards for flow cytometric analysis. They can be obtained in different narrowly defined sizes in order to standardize the FSC (standard format for flow cytometric data storage) settings. They can also be obtained conjugated to various fluorochromes in order to standardize the fluorescence detection settings.

Channel: Channel is the term by which a flow cytometer characterizes the intensity of the signal emitting by a particle. Most cytometers divide intensity of light signals into 256 for 1024 channels. Signals with high channel numbers are brighter than signals with low channel numbers; however, the quantitative relationship between signals defined by one channel number and those defined by another will depend on the amplifier and photodetector voltage characteristic of a given protocol.

Coaxial flow: The flow of a narrow core of liquid within the center of a wider stream. Flow of this type is important in flow cytometry because it provides a means by which particles flowing through a relatively wide nozzle can be tightly confined in space, allowing accurate and stable illumination as they pass one by one through a light beam.

Compensation: Compensation is the ability of a flow cytometer to correct for the overlap between the fluorescence spectra of different fluorochromes. Without compensation, fluorescence from a given fluorochrome may register to some extent on a photodetector assigned to the detection of a different fluorochrome.

Coulter volume: The increase in electrical resistance that occurs as a particle displaces electrolyte when it flows through a narrow nozzle is the particle's Coulter volume. This increase in resistance is only roughly related to the volume of the particle.

Core: The core is the stream-within-a-stream that has been injected into the center of the sheath stream and is maintained there by the hydrodynamic considerations of laminar flow. The core contains the sample particles that are to be analyzed in the flow cytometer.

Cross-talk: Cross-talk is the signal from the "wrong" photodetector that results because the fluorescent light emitted by one fluorochrome contains some light of a wavelength that gets through the filters on the photodetector that is normally specific for the fluorescence from a different fluorochrome. See "Compensation."

CV: The coefficient of variation is defined as the standard deviation of a series of values divided by the mean of those values. It is used in flow cytometry to describe the width of a histogram peak. Where in some protocols it can be used to assess the variation in particle characteristics within a population. In DNA analysis (where all normal particles are assumed to have identical characteristics), it is frequently used to assess the alignment of a flow cytometer (and the skill of the operator).

Fixation: A process by which the protein of cells is denatured. Fixation in flow cytometry is used to inactivate hazardous biological material and also to preserve stained cells where there is not immediate access to a flow cytometer. Paraformaldehyde is the fixative of choice for flow cytometry because it preserves the forward and side scatter characteristics of cells (but causes some increase in their autofluorescence).

Flow Cell: The flow cell is the device in the flow cytometer that delivers the sample stream to the center of the sheath stream. In some cytometric configurations, the illumination occurs "in air" after the stream has left the flow cell.

Fluorochrome: A fluorochrome is a dye that absorbs light and then emits light of a different color (always of a longer wavelength).

Forward scatter: Forward scatter is light from the illuminating beam that has been bent (refracted or otherwise deflected) as it passes through a particle so as to diverge from the original direction of the beam. The intensity of the light bent to a small angle from the illuminating beam is related to the refractive index of the particle as well as to its cross-sectional area. The forward scatter signal is not correlated with a cell's volume.

Gain: Gain is the electronic control on an amplifier that determines the current intensity that results when a given signal is received by a photomultiplier tube. Variation in the gain on photomultiplier tube amplifiers may vary the appearance of the output signals as they are converted into flow cytometric data.

Gate: Gate is a restriction placed on the flow cytometric data that will be included in subsequent analysis. A live gate restricts the data that will be accepted by a computer for storage; an analysis gate simply excludes certain stored data from a particular analysis procedure. A gate is used to restrict analysis of a mixed population to certain cells within that mixed population.

Granularity: Granularity is a term used synonymously with side scatter to describe the light that is deflected to a right angle from the illuminating beam in a flow cytometer. The intensity of this light is related, in an imprecise way, to internal or surface irregularities of the particles' flow through the beam.

Light scatter: Median angle light scatter (MALS) is defined as that light scatter information obtained at angles between 10° and 70°. Low angle light scatter (LALS) is light scatter information obtained at angles below between 10° relative to the beam axis, excluding 0°. High angle light scatter (HALS) is light scatter information centered at 90° to the laser axis.

Linear amplifier: A linear amplifier is one means of increasing the signal from a photomultiplier tube to make it measurable. A linear amplifier increases the signal in such a way that the output current from the amplifier is directly proportional to the input current derived from the photodetector.

Logarithmic amplifier: Logarithmic amplification is one means of modifying the signal from a photomultiplier tube to make it measurable. A logarithmic amplifier modifies the signal is such a way that the output current from the amplifier is in proportion to the logarithm of the input current derived from the photodetector.

Photodetector: A photodetector is a device that senses light and converts the energy from that light into an electrical signal. Within the operating range of the detector, the intensity of the electrical signal is proportional to the intensity of the light. Photomultiplier tubes and photodiodes are two types of photodetectors.

Photodiode: A type of photodetector used to detect relatively intense light signals. It does not have a high voltage applied to increase the current flow at its anode (output) end.

Photomultiplier tube: A photomultiplier tube is a type of photodetector used to detect a relatively weak signal. Its output current is increased by means of high voltage applied.

Rotated light scatter: Rotated light scatter (RLS) is a transformation of the data derived from a ratio of the MALS/DC pulse peak information. The RLS function has the effect of removing the size component of the cell, yielding a measurement which is more related to the internal structure of the cell.

Sheath: Sheath is the fluid within which the central sample core is contained during coaxial flow from or within the flow cell of a flow cytometer.

Side scatter: Side scatter is light of the same color as the illuminating beam that bounces off particles in that beam and is deflected to the side. The "side" is usually defined by a lens at right angle (orthogonal orientation) to the line of the laser beam. It may also be alternatively called right angle light scatter or 90° LS. The intensity of this light scattered to the side is related in a general way to the roughness or irregularity of the surface or internal constituents of a particle.

Spatial position: Spatial position is the position of the analyzed population in the domain of analysis. In the example of a VCS instrument, the domain of analysis is volume measured by D.C. current, high frequency (RF) size and light scatter. Another example is that if the analyzed population is only by volume measured by D.C. current, the spatial position would be the mean position of the analyzed population within the D.C. domain.

Threshold: The threshold is an electronic device by which an ADC can be made to ignore signals below a certain intensity. A forward scatter threshold is most commonly used in flow cytometry to exclude very small particles, debris and electronic or optical noise from acquisition.

VCS technology: An instrument that analyzes blood by using DC (Coulter) volume, Coulter opacity or RF size, and light scatter at various angular ranges.

Wavelength: A wavelength is a characteristic of light that is related exactly to its energy content and also (with light to which our eyes are sensitive) to its color. Light of short wavelength has more energy than light of longer wavelength.

Current multiple white blood cell population analysis requires analogs of specific size and volume increments and specific light scatter characteristics for use as a quality control. In the method of this invention, it is necessary to prepare at least one analog of the major leukocyte components which are the lymphocytes, monocytes, neutrophils, and eosinophils in order to check the threshold settings of electronic optical particle counters. Preferably, for the method of this invention, at least a neutrophil analog needs to be prepared. More preferably, a neutrophil and a lymphocyte analog needs to be prepared. Prior hereto, an increased volume was correlated with an increased light scatter which impeded the making of at least four different populations of leukocyte analogs from other than human white blood cells. As the analogs and instruments used to analyze the analogs have become more complex, the suspension media for the analog has to compliment their complexity. More specifically, the suspension media must be compatible with these analogs and instruments, and compliment the physical and biological properties of the analogs.

The suspension media is primarily used with leukocyte analogs produced from blood cells. One process to produce leukocyte analogs provides treated blood cells from different sources to match a plurality of threshold settings for many types of blood counting instruments. In the selection of the blood cells, the main limitation is the mean cell volume of the original cells as it relates to the mean cell volume of the desired analog. Without limiting the scope of this method, specific reference will be made to blood cells from particular animals, with the understanding that red and white blood cells from other animals may be employed in the method of this invention.

One process for the manufacture of the leukocyte analogs that are useful in the method of this invention comprises mixing a red blood cell with a hypoosmotic solution to expand the volume of the cell; changing the hemoglobin content of the cell to simulate the light scatter and opacity properties of human leukocyte cells; and, fixing the cell so that it is resistant to degradation by lytic reagents used in the hematological test procedure and said fixed cell having at least two properties selected from the group comprising volume measured by D.C. current, high frequency (RF) size, opacity and light scatter similar to human leukocytes properties. The process for making the eosinophil blood cell analog is similar, but the changing of the hemoglobin content is accomplished by denaturing it in the cell rather than leaking it from the cell. This additional embodiment results in an analog having volume and light scattering characteristics of a human leukocyte.

This process also enables the swelling of red blood cells greater than 50% of their original volume, which provides a wider latitude in the selection of animal cells for producing the desired analogs. In a preferred process, the red blood cells are swollen greater than 75% of their original volume.

For the purpose of making analogs suitable for use with the method of this invention, it has been found that fowl red blood cells such as turkey, chicken, duck, and preferably goose red blood cells, lend themselves to an aldehyde stabilization process to produce the smaller lymphocyte analogs. It has also been found that other non-human vertebrates including "fishes", particularly members of the shark family, and reptiles, preferably alligators, have red blood cells in the desired size range which when properly treated yield in an analog similar to the larger sizes of the human monocytes, neutrophils and eosinophils. These erythrocytes generally show excellent suspension stability and highly reproducible volume distribution characteristics. However, considerations, such as availability in quantity at reasonable expense, must be considered.

Moreover, the red blood cells are fixed so that they are resistant to degradation by the lytic reagent used in the hematological test procedures when determining the white blood cell parameters in the whole blood control product.

The cells of avian, alligators and nurse sharks, are nucleated, but the presence of a nucleus is neither essential nor detrimental for their use as a substitute for human white blood cells, given the process described herein which permits a regulated hemolysis of the red blood cell. Preferably between 20% to 80% by weight and most preferably 30% to 70% by weight of the hemoglobin in the cell is released. The cells are further stabilized with a fixing agent, such as an organic aldehyde which prevents disruption of the cell membrane and further loss of hemoglobin.

Another process for the manufacture of the leukocyte analogs that are useful in the method of this invention includes the stabilizing of human white blood cells to simulate at least one of the five subpopulations of leukocytes.

In addition, the method of this invention is useful with leukocyte analogs prepared by other processes known in the art. These stabilized leukocyte analog cells provide a satisfactory substitute for human leukocyte cells in a control product.

A preferred process to produce a control product suitable for use in the method of this invention, embodies a composition prepared by mixing a suspension of fixed goose red blood cells to simulate human lymphocytes, fixed alligator red blood cells to simulate human monocytes, neutrophils, and eosinophils, all assembled in the suspension media and in such proportions as to provide a single composition to simulate human white cells. This control product then is commingled with lysable human red blood cells, and stabilized platelets or platelet analogs, to provide a single multiple-analysis control product.

The following description describes a preferred process of making a control product using red blood cells for use in the method of this invention.

In the collecting step, the red blood cells are suspended in an anticoagulant, such as an alkali metal salt of ethylenediaminetetraacetic acid (EDTA) dissolved in a physiological saline solution (sodium chloride). It is envisioned that other anticoagulants and salts will do, as long as they do not cause undue hemolysis or cell association.

Fresh red blood cells must be washed to remove donor specific plasma proteins. This will reduce the probability of cell agglutination when mixing red cells from multiple blood cell donors. The cells are pooled together to obtain a homogeneous composite.

The cell pool may be pretreated with a serum substance as a processing aid. The pretreatment with the serum substance permits swelling of the cell without causing the cell to rupture. Exposure of the erythrocytes to a hypoosmotic environment has the principal effect of increasing the mean corpuscular volume, and decreasing the widths of the light scatter histogram. The blood cells are increased in size as a result of the hypoosmotic environment having a solute concentration which is reduced from the solute concentration of the cells. When the concentration of solute inside the cell is greater than the concentration outside the cell, there is a tendency for the water to move into the cell to equilibrate concentration. As such, the moving of water inside the cell causes swelling. The hypoosmotic environment can include a solution of sodium compounds, potassium compounds, or both sodium and potassium or other compositions known to those skilled in the art to provide the desired solute concentration.

As defined herein, serum comprises cholesterol, cholesterol esters, and cholesterol which has been combined with one or more other compounds found in serum plasma, and mixtures thereof. Preferably, such other compounds further comprise lipoproteins and phospholipids, and mixtures thereof. As appreciated by those skilled in the art, typically cholesterol will contain approximately 30% esters. As further appreciated by those skilled in the art, the lipoprotein will maintain the cholesterol in an aqueous solution. Preferably, the serum substance in the pretreatment is selected from the group comprising cholesterol, cholesterol esters, lipoprotein cholesterol, lipoprotein cholesterol esters, cholesterol combined with phospholipids and mixtures thereof. Most preferably, the serum substance comprises cholesterol in combination with phospholipids. A suitable commercially available example of such preferred embodiment is Pentex® Cholesterol Super-Trate by Miles, Inc., which is a high density lipoprotein cholesterol and lipoprotein cholesterol esters in combination with phospholipids. Thus, when smaller cells are expanded greater than 30% to 50% of their original volume, the pretreatment is necessary. It is further believed that the concentration of the serum substance used is both a function of the amount of cell expansion, caused by the hypoosmotic solution, as well as, the process conditions of the fixation reaction which permits the cell's hemoglobin to leak from the cell. In processes which fix the cell in less than approximately 2 hours due mainly to the aldehyde concentration at room temperature, and wherein the hypoosmotic pressure is greater than approximately 150 milliosmoles, no pretreatment appears necessary. When the pretreatment is used, preferably the concentration of the cholesterol is from 0.1 to 5.0 milligrams to a cell count of $1 \times 10^6$ cells per microliter. If too high of a cholesterol concentration used, then the cells will tend to lyse. If too low of cholesterol concentration is used, the cell will rupture when swelled.

Prior art attempts at swelling cells without bursting them have focused on the use of a processing aid, such as potassium sodium tartrate, which functions to strengthen the cell membrane. However, this approach does not permit expansion greater than the expected 30 to 50%, nor provide the cell with regulated hemolysis.

Although the present process is disclosed in terms of simultaneously swelling and fixing of the cell in a one step process, it is within the contemplation of this process that more than one step could be used to pretreat the cell with the serum substance, swell the cell to permit a controlled release of hemoglobin and thereafter fix the cell. However, such procedure would be expected to have the problems of controlling the process conditions for each step, and more specifically, the timing of the fixation of the blood cell.

In a preferred process to produce the control product for use in the method of this invention, the hypoosmotic solution is formed by combining an aqueous solution of sodium phosphate with the fixative reagent to the desired osmotic pressure. The lower the osmotic pressure relative to the normal tonicity of the native blood, the more that the cell will swell due in part because of the water moving from outside the cell to inside the cell. The osmotic pressure will preferably range from 0 to 150 milliosmoles, depending upon the initial cell size, cell count, and the desired final cell size; even more preferably from 65 to 95 milliosmoles for the eosinophil analog; 0 to 20 milliosmoles for the monocyte analog; 5 to 35 milliosmoles for the lymphocyte analog; and from 45 to 65 milliosmoles for the neutrophil analog. The above preferred ranges are based upon blood cells that have been washed with an isotonic saline solution and are further based upon a cell count in the fixative reaction of approximately 20,000 to 50,000 cells per microliter.

Concomitantly, temperature does not appear to independently affect the swelling rate of the cell, but does affect the rate of the fixation reaction. As the cell expands, the hemoglobin leaks out of the cell at a controlled rate until the fixation reaction prevents further release of hemoglobin. The majority of the hemoglobin will be released within the first five minutes of the hypoosmotic treatment. Thus, in the simultaneous swelling and fixing of the cells, reducing the temperature of the fixation in solution enables the control of the fixation process and hemoglobin release rates during which time the cell is swelling. Upon completion of the fixation reaction, the cell is resistant to dissolution or degradation under the influence of the usual lysing reagents used in hematological test procedures.

In a further process to produce control products for use in the method of this invention, the blood cells are added to a chilled hypotonic solution containing glutaraldehyde. The chilled fixing solution is at a temperature of 0° to 15° C., and more preferably, from 1° to 10° C., most preferably, the fixation treatment is at 2° to 8° C. for the lymphocyte and monocyte analogs and at room temperature for the neutrophil and eosinophil analogs. The reduced temperature has been shown to provide a qualitatively different cell as measured on a sizing apparatus such as a COULTER COUNTER® Model VCS analyzer. A qualitative difference includes a higher mean cell volume compared to fixing at room temperature.

Fixing of the swollen cells is important to toughen the cell membranes and to prevent degradation of the membranes. This is accomplished by contacting the cells with a solution of an organic aldehyde, including monoaldehydes such as formaldehyde, or dialdehydes such as glutaraldehyde. Glutaraldehyde is the preferred aldehyde, since it reacts more speedily than formaldehyde. Glutaraldehyde can be added in higher concentrations than the final concentration, so long as the final concentration is in the range of about 0.05% to 0.8% and more preferably 0.1% to 0.6%, based upon a cell count of approximately 20,000 to 50,000 cells per microliter. The practical limitations on selection of an appropriate aldehyde and concentration thereof are the functional limitations of the number of cells, elimination of undue cell association, and as a parameter in controlling the fixation reaction. The fixation reaction conditions will vary for the specific animal cell used and the leukocyte analog being manufactured.

Although most room temperature fixation with glutaraldehyde occurs within two hours, more time is required for the red blood cells to be totally resistant to the usual red blood cell lytic agents employed in COULTER COUNTER® hematology instruments. With careful selection of the red blood cells, the length of time for fixation with glutaraldehyde will range between 2 and 72 hours, preferably between 3 to 30 hours, depending upon temperature, concentration of glutaraldehyde, number of cells and desired amount of hemoglobin released. In a most preferred embodiment, the fixation time for a cell count of approximately 20,000 to 50,000 cells per microliter is between 10 to 24 hours for the monocyte and lymphocyte analogs and 3 to 18 hours for the eosinophil and neutrophil analogs. Under-fixation may result in a partially fixed red blood cell with a mean cell volume less than that for the targeted human leukocyte population. Generally, the upper time limit of fixation is based upon manufacturing convenience. After fixation, the cells are separated from the liquid phase by a centrifugation or gravitation means and then are washed with a phosphate buffered saline solution.

The pH of the fixing solution ranges from 7.0 to 9.0. If the pH of the fixing solution is too low, agglutination may occur; and if too high, the cell may rupture. In addition, the pH affects the release of hemoglobin. If the fixation reaction occurs too quickly, the cell will not be able to leak the hemoglobin. Thus, the pH range is approximately 7.0 to 9.0, and preferably 7.5 to 8.5. In a most preferred embodiment, the pH of the fixation solution is 8.0±0.2 for the neutrophil and eosinophil analogs, and 7.8±0.1 for the monocyte and lymphocyte analogs.

The eosinophil analog is prepared in a similar process except, the hypotonic glutaraldehyde solution is preferably at room temperature and the hypotonic glutaraldehyde solution is primarily used to lightly cross link the hemoglobin in the blood cells, rather than to completely fix the cell. As such, the glutaraldehyde concentration for a cell count of approximately 20,000 to 50,000 cells per microliter is between approximately 0.1 and 0.4%, and more preferably from 0.2 to 0.3%. After lightly cross linking the hemoglobin and washing with a phosphate buffered saline solution, the cells are further treated with a protein denaturing reagent, such as a quaternary ammonium compound, or other denaturing agent known to those skilled in the art to precipitate the hemoglobin within the cell. The pH of the denaturing solution should be between 9.0 and 12.0, and preferably between 10.0 and 11.0. This treatment does not reduce the volume of the cell. The treatment with the protein denaturing reagent increases the light scatter characteristics of the swollen cell to provide the swollen cell with the requisite light scattering characteristics similar to the human eosinophil. Both the denaturation of the hemoglobin and the controlled release of the hemoglobin have the effect of changing the hemoglobin composition in the cell. However, the light scatter properties are distinctly different between the controlled release of the hemoglobin in the monocyte and lymphocyte analogs and the denaturation of hemoglobin in the eosinophil analog. Generally, the leaking of hemoglobin from the cell will reduce the light scatter and opacity of the cell. Denaturing the hemoglobin in the cell will increase the light scatter of the cell.

The preferred process of preparing the eosinophil analog comprises pretreating the red cell pool with an aqueous serum substance, swelling the cell, denaturing the hemoglobin in the cell and fixing the cell. As appreciated by one skilled in the art, it is within the contemplation of this process to produce a control product that one could choose an appropriate sized red blood cell which did not require the amount of swelling which would necessitate the pretreatment with the serum substance. In such case, the process would comprise denaturing the hemoglobin in the cell to simulate the light scatter properties of a human leukocyte cell and fixing the cell so that it is resistant to degradation by lytic reagents used in hematological test procedures. As such, the treated red cell would have light scatter and volume properties similar to human leukocytes. However, if the cell is not swelled to some extent, it would be expected that since the red blood cell is not by nature spherical, the standard deviation of the light scatter would not be within boundary of the targeted cell population. The addition of a sphering agent may obviate this problem.

By using a combination of the above disclosed processing steps, of swelling the cell, leaking of hemoglobin from the cell, denaturing the hemoglobin in the cell, as well as, shrinking the cell by processes known to those skilled in the art, one is effectively provided with processes to design an analog having a plurality of different physical parameters of D.C. volume, RF size, opacity and light scatter which can be used in new methods to diagnose the cause of a malfunction of an instrument. More specifically, shrinking and swelling of the cell can affect all of the above listed parameters, while changing the hemoglobin in the cell can affect the opacity and light scatter characteristics.

The suspension media disclosed herein, is also used with leukocyte analogs prepared by other processes known in the art. One such other process includes the fixing of human white blood cells to simulate five subpopulations of leukocytes as described in Example 5 herein.

The reference blood cell control product can include one or more of the leukocyte analogs prepared by any process known to those skilled in the art or any of the above described processes. The leukocyte analog can be stored in any suitable media such as phosphate buffered saline solution and those fully described in U.S. Pat. Nos. 4,213,876; 4,299,726, 4,358,394 and 3,873,467.

The following specific example is disclosed in U.S. Pat. No. 4,299,726:

Stabilizing Media for Conferring Long Term Stability on Red Blood Cells-Preferred Formulation

| Approximate Amounts | Liter Formulation |
|---|---|
| 1. Distilled water | 500 ml |
| 2. Propyl paraben | 0.3 to 1.0 gm |
| 3. Methyl paraben | 0.5 to 1.0 gm |
| 4. Procaine hydrochloride | 0.1 to 0.5 gm |
| 5. Deoxycholic acid | 0.1 to 0.9 gm |
| 6. Lactose | 10.0 to 50.0 gm |
| 7. Actidione | 0.1 to 0.6 gm |
| 8. Trisodium citrate dihydrate | 3.0 to 8.0 gm |
| 9. Citric acid monohydrate | 0.3 to 0.9 gm |
| 10. Sodium dihydrogen phosphate monohydrate | 0.8 to 2.5 gm |
| 11. Phenergan hydrochloride | 0.1 to 1.0 gm |
| 12. Colistimethate, sodium | 0.2 to 0.9 gm |
| 13. Penicillin G., sodium | $0.5 \times 10^6$ to $3 \times 10^6$ units |
| 14. Kanamycin sulfate | 0.2 to 0.8 gm |
| 15. Neomycin sulfate | 0.2 to 1.0 gm |
| 16. 5'-AMP | 0.4 to 1.0 gm |
| 17. Adenine | 0.2 to 0.8 gm |
| 18. Inosine | 0.4 to 1.0 gm |
| 19. Dihydrostreptomycin sulfate | 0.2 to 1.0 gm |
| 20. Tetracycline hydrochloride | 0.2 to 1.0 gm |
| 21. 30% Bovine albumin | 100 to 350 ml |
| 22. q.s. to 1 liter with distilled water | |

Since many of the chemicals listed above are known commercially by several names, the name given is a common name listed in the Merck Index, Eleventh Edition (1989), published by Merck and Co., Inc., Rahway, N.J.

When making the control product, the supernatant fluid is removed from the leukocyte analogs and they are then resuspended in the suspension media. The preferred suspension media comprises an aqueous solution of a plasma substance. As defined herein, an aqueous solution of a plasma substance comprises an aqueous solution of a serum substance (as previously defined), serum substance in combination with a plasma protein and mixtures thereof. As further defined herein, plasma protein comprises one or more of the proteins contained in plasma. Preferably, such plasma proteins comprise albumin, lipoproteins, globulins, fibrinogens, and mixtures thereof. More preferably, the plasma substance is selected from the group comprising cholesterol, cholesterol esters, lipoprotein cholesterol, lipoprotein cholesterol esters, cholesterol combined with phospholipids, cholesterol combined with albumin, cholesterol esters combined with albumin, lipoprotein cholesterol combined with phospholipids, lipoprotein cholesterol combined with albumin, and mixtures thereof.

To confirm the utility of the plasma substance for red blood cell lysis in a saponin based lytic system, an aqueous plasma substance was added to washed red blood cells. The aqueous solution comprised 3% plasma substance in a phosphate buffered saline solution. The results are as follows:

| Sample | Plasma Substance | Lysis |
|---|---|---|
| 1. | Human albumin | Yes |
| 2. | Albumin with fatty acid removed | No |
| 3. | Sample 2 with lipoprotein cholesterol | Yes |
| 4. | Bovine serum albumin | No |
| 5. | Sample 4 with lipoprotein cholesterol | Yes |
| 6. | Albumin bound cholesterol | Yes |
| 7. | Monomer albumin | Yes |
| 8. | Bovine serum albumin capalate stabilized | No |
| 9. | Sample 8 with lipoprotein cholesterol | Yes |
| 10. | Polymer enhanced bovine serum albumin | Yes |
| 11. | Human albumin | Yes |
| 12. | Swine albumin | Yes |
| 13. | Media of U.S. Pat. No. 4,299,726 | No |
| 14. | Sample 13 with lipoprotein cholesterol | Yes |
| 15. | Cholesterol bound with a surfactant | No |
| 16. | Phosphate buffered saline (PBS) solution | No |
| 18. | Lecithin | No |
| 19. | PBS with lipoprotein cholesterol | Yes |

From the test results given above, it has been determined that the addition of a plasma substance to washed red blood cells enables lysis in a saponin lytic system. It is believed that the albumin is interacting with the red blood cell and saponin to effect the lytic action. However, when the washed red blood cells and bovine serum albumin are further combined with other ingredients such as those disclosed in U.S. Pat. No. 4,299,726, the albumin does not cause the lysis. However, when a lipoprotein cholesterol is added, lysis is effected. Moreover, when a lipoprotein cholesterol is added to the PBS, lysis is effected.

When using the leukocyte analogs prepared from red blood cells as described above, the aqueous solution of a plasma substance is preferably added to the hematological composition at least 12 hours before being used in an instrument. When one or more leukocyte analogs are combined with lysable human red blood cells to provide a single multiple analysis reference blood cell control product for instruments which use lytic reagents, it is most preferred that the aqueous solution of the plasma substance comprises bound cholesterol. A suitable example of the most preferred plasma substance is Moducyte®, as described in U.S. Pat. No. 4,290,774, assigned to Miles, Inc., which is a high density lipoprotein cholesterol bound with albumen. The final concentration of cholesterol in the suspension media ranges from 400 to 1,200, and preferably 600 to 1,000 milligrams per liter depending upon the cell count in the final control product.

For a control product using the leukocyte analogs prepared by the preferred processes disclosed herein, if an insufficient concentration of the cholesterol is used in the preferred media, the red blood cells in the reference blood cell control product will not efficiently lyse to dissolve the cell membrane so that there is an absence of noise and debris when using a saponin lytic reagent system and the leukocyte analogs will have a mean cell volume below the required size due to the lytic reaction. If the media contains too high of a concentration of cholesterol, the red blood cells in the reference blood cell control will not efficiently lyse to dissolve the cell membrane so that there is an absence of noise and debris.

More specifically, when the control product is used in instruments, such as those that employ the Coulter Model VCS technology, which uses a reagent system such as described in U.S. Pat. No. 4,751,179, in order to distinguish at least two populations of leukocytes, (1) lymphoids (lymphocytes) and (2) myeloids (neutrophils, monocytes, eosinophils and basophils), the preferred suspension media enables the reaction between the weaker lytic reagent and the non fixed red blood cells to occur so that the red blood cells lyse while the leukocyte analogs remain substantially unaffected, enabling each type of leukocyte analog to be counted. As taught by U.S. Pat. No. 4,751,179, the lysing reagent has two forms: (1) a lytic diluent containing saponin, which simultaneously functions to dilute the whole blood sample and stromatolyse its red blood cells; or (2) a two part system comprised of non-lytic blood diluent followed by a lytic reagent containing saponin.

When prior art medias, such as those described in U.S. Pat. No. 4,213,876; 4,299,726; or 4,358,395, are used, the leukocyte analogs prepared by the preferred processes disclosed herein are lower in volume than desired for the targeted leukocyte population. More specifically, when the preferred suspension media is used with leukocyte analogs, which have been prepared from either red or white blood cells, the D.C. volume of the analog is within the desired range for the targeted leukocyte population.

In a more preferred embodiment, the suspension media would further comprise the addition of a non-ionic surfactant. The surfactant will have a high hydrophile-lipophile balance (HLB). The HLB typically has a value greater than 15 and more preferably greater than 17. Typically, the surfactant is in an amount effective to make the lytic action more specific to the red blood cells without detrimentally affecting the leukocyte analogs. In addition, the surfactant will stabilize any free cholesterol in the control product so that it does not separate out in solution. As appreciated by those skilled in the art, the effective amount of surfactant may be empirically determined, but is typically less than 0.5% by weight of the control product. polyether alcohols of the general formula: R—X—(y)$_n$—H, where R is alipophilic chain $C_8$–$C_{18}$ carbon atoms; where X is —O—,

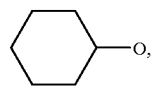

—COO—; and Y is $CH_2$ $CH_2O$— or $CH_2$ $CH_2$ $CH_2O$; n is an integer of 15–50. Suitable commercial examples of these surfactants include Diazopan® SS-837 by GAF Chemical Corp., Triton® X405 by Rohm and Haas, and Pluronic F®-127 PRILL by BASF Wyandotte Corp.

While not desiring to be bound by any theory, it is presently believed that there is an interaction among the red blood cells, weak lytic agent (e.g., saponin), and the plasma substance in the preferred suspension media causes the red blood cells to lyse. More specifically, it is presently believed that the plasma substance may be affecting the cell membrane cholesterol which further affects the leukocyte analog's response to the lytic reagent. Moreover, it is further believed that the surfactant makes the lytic reaction more specific to the red blood cells and yet does not detrimentally affect the leukocyte analogs as to measured control parameters. In addition, it is further believed that the surfactant may also be affecting the cholesterol found in the cell membrane or in the plasma substance.

The preferred suspension media for the hematological reference control product having stability up to six months includes an aqueous solution of the plasma substance and optional compatible fungicidal and bactericidal agents, and optional supplementary agents such as purine nucleoside, bile salt, and cholic acid derivatives, phenothiazine compounds and the salts thereof having antihistamine properties, and 4-aminobenzoic acid esters and derivatives and their salts having aesthetic properties, as well as, sphering agents for the red blood cells, or combinations thereof. Since one or more of the leukocyte analogs may be combined into a single reference blood cell control product for use with the known lysing agent for the red blood cells, the formulation for the preferred suspension media is the same for all of the leukocyte analogs.

As appreciated by one skilled in the art, the suspension media should have sufficient tonicity to avoid cell lysis. The preferred formula for the suspension media is:

| Suspension Media | | |
|---|---|---|
| Approximate Amounts | | Liter Formulation |
| 1. | Distilled water | 500 ml |
| *2. | Propyl paraben | 0.3 to 1.0 gm |
| *3. | Methyl paraben | 0.5 to 1.0 gm |
| *4. | Procaine hydrochloride | 0.1 to 0.5 gm |
| *5. | Deoxycholic acid | 0.1 to 0.9 gm |
| *6. | Lactose | 10.0 to 50.0 gm |
| *7. | Actidione | 0.1 to 0.6 gm |
| *8. | Trisodium citrate dihydrate | 3.0 to 8.0 gm |
| *9. | Citric acid monohydrate | 0.3 to 0.9 gm |
| *10. | Sodium dihydrogen phosphate monohydrate | 0.8 to 2.5 gm |
| *11. | Phenergan hydrochloride | 0.1 to 1.0 gm |
| *12. | Colistimethate, sodium | 0.2 to –0.9 gm |
| *13. | Penicillin G., sodium | $0.5 \times 10^6$ to $3 \times 10^6$ units |
| *14. | Kanamycin sulfate | 0.2 to 0.8 gm |
| *15. | Neomycin sulfate | 0.2 to 1.0 gm |
| *16. | 5'-AMP | 0.4 to 1.0 gm |
| *17. | Adenine | 0.2 to 0.8 gm |
| *18. | Inosine | 0.4 to 1.0 gm |
| *19. | Dihydrostreptomycin sulfate | 0.2 to 1.0 gm |
| *20. | Tetracycline hydrochloride | 0.2 to 1.0 gm |
| *21. | 30% Bovine albumin | 100 to 350 ml |
| 22. | Lipoprotein Cholesterol | 400 to 1,200 mg |
| 23. | q.s. to 1 liter with distilled water | |

*Optional ingredient preferred for conferring long term stability for red blood cells and analogs.

The manufactured control product can be used to monitor and diagnose the cause of a malfunction of an instrument. In this invention, a method for using a hematology control product has been developed that enables the monitoring and diagnosing of an instrument for problems associated with:

1. lysis debris and noise
2. instrument reagents pump volume settings
3. instrument laser alignments
4. instrument gain settings
5. inconsistency of flow rate in the flow cell The method provides a more specific indication of the type and cause of an instrument malfunction than non specific flagging that is diagnostically non specific or inspection of the test results by the instrument operator which are provided by prior art methods. The following description describes a new method of using the previously described control product. As appreciated by one skilled in the art, the control product must contain lyseable erthryocytes to monitor any cellular debris and noise caused by ineffective red cell lysis. The method uses new control parameters of the physical properties of the control product to determine the cause of an instrument malfunction. These physical properties are selected from the group comprising:

(1) volume measured by D.C. current,
(2) high frequency (RF) size,
(3) opacity, and
(4) light scatter.

The leukocyte populations are used as the indicator of system performance. Preferably the neutrophil and lymphocyte subpopulations are used as control parameters and are measured to determine instrument performance. More preferably the neutrophil population is used as a control parameter and is measured as an indication of system performance.

In order to determine whether there is a noise problem due to cellular debris, the use of two control parameters are employed. The control parameters are COUNT RATIO and ELAPSED TIME. The COUNT RATIO is a measure of the number of white blood cells in an analysis compared to the total count of events that are recorded in the analysis during a specific ELAPSED TIME. ELAPSED TIME is a measured period of time, usually in seconds. As the ratio of white blood cells counted and total event counted approaches 100 percent, the cellular debris or noise problem associated with an instrument malfunction is eliminated.

An example of the use of COUNT RATIO in an instrument employing VCS technology would be a comparison of the number of white blood cells analogs compared to a total count of 8192 particles obtained for a specific ELAPSED TIME. If the ratio is less than about 95%, there its an indication that noise or interference is a problem. The specific problem is further confirmed by additional tests that are further explained in this disclosure.

Another approach to monitor and diagnose an instrument for problems is to use fresh blood monitoring of the running average of the same set of parameters of a statistically significant number of patient normal bloods. When the average is outside the expected ranges of the control parameter there is an early indication of the instrument malfunction. The instrument malfunction can be further verified using the control product described herein.

One indication of whether an instrument is properly functioning is to determine the cellular debris or noise that is measured by the instrument. Excess cell debris can be caused by incomplete lysis, changes in the reaction kinetics due to temperature conditions or interference with the lytic reaction. Since various instrument systems have cell count and data accumulation time limitations, excess debris or noise from any source interferes with the proper acquisition and analysis of the white cell populations. The cause of the cellular debris or noise problem can be attributed to several problems including:

A. conductivity noise due to sheath fluid and the blood sample stream imbalance.
B. Lysing noise caused by improper red cell lysing.
C. Flow noise caused by partial plugs, residual plugs or other flow problems In order to determine whether the malfunction is due to conductivity noise caused by mismatches between the sample stream and the sheath fluid stream conductivity, one first measures the reagent pump volumes. A calibrated container is employed to measure each of the reagents that are added to the blood sample. The volume of reagent that is transferred should be within a predetermined value. If the volume of a reagent is not within the prescribed limits, then the reagent pump is adjusted to increase or decrease the reagent volume that will be dispensed.

In the example of an instrument that employs VCS technology, one measures the pump volumes of the lytic reagent and quench reagent streams. A calibrated container is employed to measure each of these volumes. The volume of the reagent should be within a predetermined value. If the volume of the reagent is not within the prescribed limits, then the pump is adjusted to increase or decrease the volume that will be provided.

The prepared control product containing fixed cell analog populations that are osmotically sensitive are further used to monitor the reagent pump volumes. Changes in volume of lytic reagents will affect the final osmolality of the diluted blood sample and affect the measured volume of the analog population. Lower osmolality increases the measured volume of the control cell analog and higher osmolality decreases the measured volume of the control cell analog. Variations of reagent pump volumes beyond the limits of conductivity required to electrically balance the sheath fluid will produce noise in addition to the changes in the volume of the control cell.

Therefore, after the conductivity noise has been minimized by the preceding process, lysing noise resulting from improper red cell lysing is checked with a control product containing a known number of stabilized red blood cells and at least one leukocyte analog cell subpopulation. If lysing is a problem, then the control cells will show a COUNT RATIO less than about 95% of the maximum COUNT RATIO. In addition, although the reagent volumes can be adjusted by the preceding process, the lysing kinetics relating to the temperature of the lysing reaction will be affected. More specifically, it has been found that if the room temperature of a laboratory instrument is at 50° F., the lysing reaction will require a different lytic and quench reagent volume than if the temperature is at 90° F., to obtain a minimum of lysing noise.

In the example of an instrument which employs the VCS type technology, the lytic reagent and quench reagent are reacted with a blood sample to provide a lysed and diluted suspension of white blood cells suitable for measurement. In the VCS type instrument, blood cells are reacted with the lytic reagent causing hypotonic cell swelling, red cell and platelet lysis and dissolution of red cell and platelet membranes. Reaction with the quench reagent stops the swelling and lysis and begins a process of re-equilibration of the white cells to their native size. Because of the nature of the reactions, the lytic reagent and quench reagent are very different in both osmolality and conductivity. The final osmolality and conductivity of the sample stream is proportional to the volume, osmolality and conductivity of the lytic reagent, quench reagent and blood sample.

The use of two control parameters are employed to determine if the reagent pump volumes are within specification or determining the cause of the malfunction. The monitoring the COUNT RATIO and NEUTROPHIL DC MEAN assists one in differentiating pump volume changes within conductivity tolerances and beyond conductivity tolerances. The NEUTROPHIL DC MEAN is the neutrophil mean value in the DC channel.

Another approach to monitor and diagnose an instrument for problems is to use fresh blood monitoring of the running average of the same set of parameters of a statistically significant number of patient normal bloods. When the average is outside the expected ranges of the control parameter there is an early indication of the instrument malfunction. The instrument malfunction can be further verified using the control product described herein.

It has been found that the COUNT RATIO of the white blood cells is related to the reagent pump volumes calculated from known reagent concentrations and measured pump volumes, expressed as either dilution conductivity or osmolality. FIG. 1 represents a comparison of the COUNT RATIO of the white blood cells compared to the conductivity of the diluted blood sample in the diluted blood sample stream that is to be tested. As shown in FIG. 1, as the quench reagent volume is increased, the COUNT RATIO increases to a plateau. When the quench volume is increased beyond the optimum range the COUNT RATIO is substantially reduced.

To obtain a comparable FIG. 1 using a control product, the lytic reagent volume is provided at a first volume that would be expected to provide proper lysis. The quench volume is adjusted from providing insufficient quench reagent to providing an excess amount of quench reagent. When the quench reagent volume is insufficient, the COUNT RATIO is significantly reduced. As the quench volume is increased the COUNT RATIO rises and plateaus over the optimum performance range. Increasing the quench volume above the optimum range causes the COUNT RATIO to be substantially reduced. Upon obtaining this information, the pump for the quench reagent can be adjusted to provide a quench reagent volume that is in the middle of the plateau.

After the quench volume has been adjusted, the lytic reagent pump can be re-adjusted. It has been found that the NEUTROPHIL DC MEAN of the control product is related to the lytic reagent pump volume. The monocyte population shows sensitivity similar to the neutrophil population. The pump for the lyse reagent is adjusted to provide an osmolality which corresponds to a previously measured NEUTROPHIL DC MEAN of the control product. The previously measured NEUTROPHIL DC MEAN is provided as an assay value from a reference instrument.

Figure 2:
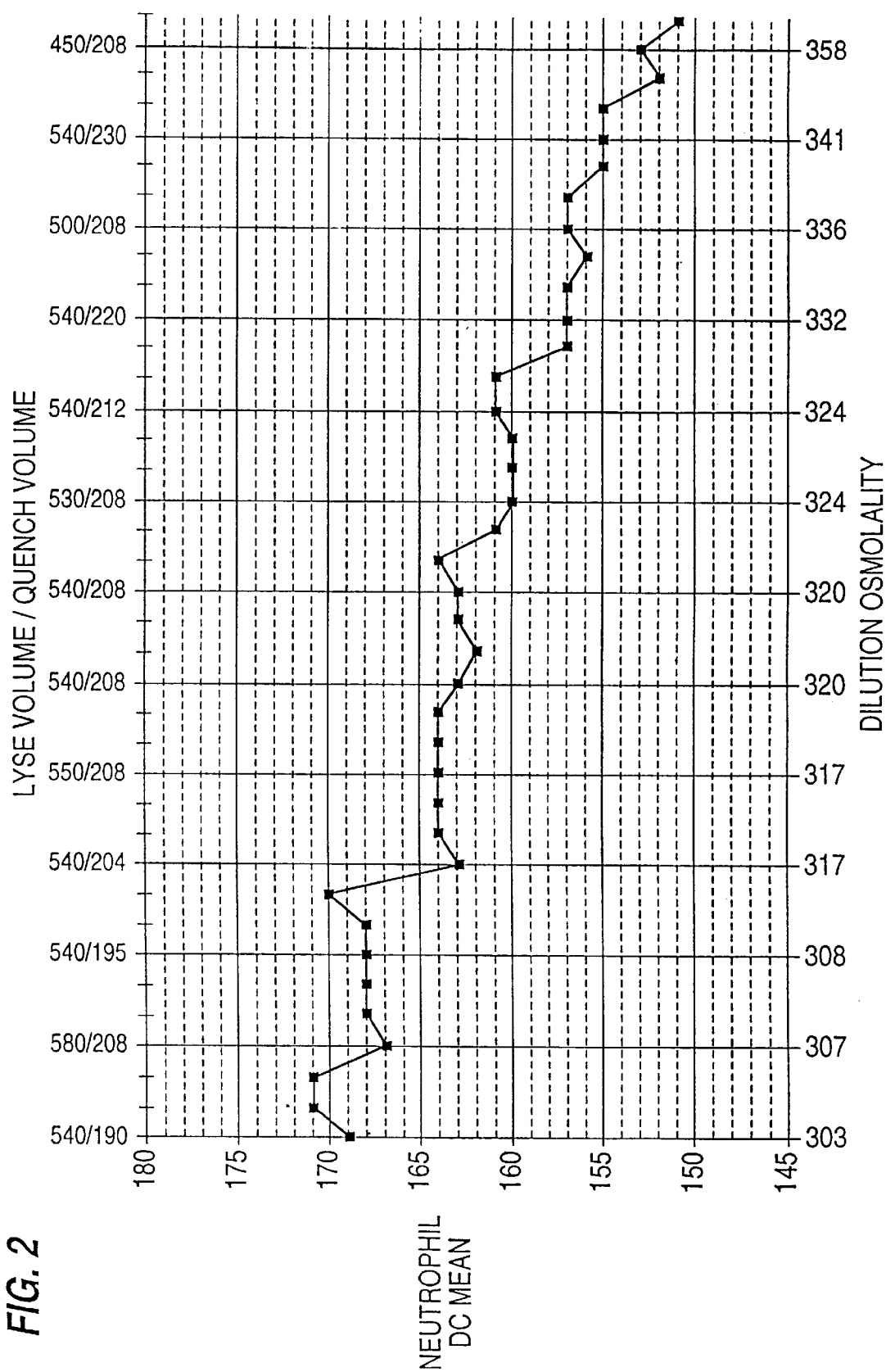
FIG. 2 is a comparison of the NEUTROPHIL DC MEAN compared to the osmolality of the blood sample being analyzed after it has been diluted with the lytic and quench reagents.

FIG. 2 represents a comparison of the NEUTROPHIL DC MEAN compared to the osmolality of the blood sample being analyzed after it has been diluted with the lytic and quench reagents. As shown in FIG. 2, as the osmolality is increased, the NEUTROPHIL DC MEAN of the control product decreases.

In order to determine whether there is a problem because of left over plugs or partial plugs, two control parameters of WHITE TIME and DATE TIME are used. The monitoring of these two control parameters assists one in determining these type of problems. WHITE TIME is the product of the number of white blood cell analogs multiplied by the time required for analysis. DATE TIME is the day that a control sample has been analyzed. It has been found that using these two control parameters on a routine basis with a control product that contains a known number of leukocyte analogs provides information as to instrument performance problems.

In the method of this invention, the control product is used at least daily. The WHITE TIME and DATE TIME are recorded to provide meaningful information about the existence of flow problems. More specifically, when the WHITE TIME is graphed versus the DATE TIME, one is able to obtain a two dimension graph of the performance of the instrument to determine trends of the flow performance of the instrument.

In a VCS type instrument, an alternate method is provided to check the sample flow rate. The VCS instrument records the WHITE TIME and DATE TIME on each patient blood sample that has been analyzed by the instrument. By comparing these control parameters on a statistically significant number of patient blood samples, an expanded data base is available to monitor the history of the instrument's flow performance. More specifically, by recording the WHITE TIME and DATE TIME on each patient blood sample, one is able to detect whether left over plugs or partial plugs have occurred. Left over plugs can restrict the flow of subsequent samples, but may produce no detectable change in the number of cells per second. Partial plugs can increase the time required to obtain the white blood cell count because of a reduced flow of cells through the flow cell.

In addition, when these control parameters are monitored for the patient samples, a two dimension analysis can be obtained to discover if the flow rate is deteriorating and whether noise and debris levels are interfering with the expected time to obtain the white blood cell count. Excessive debris will decrease the amount of time necessary to obtain a specified number of white blood cells. This two dimensional analysis has provided an improvement over complex multidimensional analysis of the prior art.

Prior art methods to determine problems due to the consistency of the flow cell has been to measure the number of leukocytes that are detected during a predetermined time. More specifically, the instrument operator would use a specially selected fresh blood that had a known number of white blood cells and measure the time the instrument required to detect the white blood cells. If the instrument detected the white blood cells within a specified time, it was presumed that there was an absence of flow cell problems. However, this measurement only provided information about the instrument for that particular analysis. This measurement did not provide meaningful information concerning the performance of the instrument over an extended time period. More specifically, graphing the count of white blood cells per unit time only provides an instantaneous view of the instrument's performance on that one day. To obtain a view of the performance of an instrument over several days, a three dimensional charting of the results was necessary. Moreover, the method of this invention uses a control product with a known number of white blood cells which eliminates the necessity of obtaining a specially selected fresh blood and determining the number of white blood cells it contains.

In addition, a control product can be used to monitor the instrument to determine if there is a problem with the instrument's laser, the laser optics or the laser alignment. Laser alignment has three dimensions which corresponds to X, Y and Z axes.

Currently, the material used to set and then monitor laser alignment and gain adjustments is latex microparticles. The method of using the latex particle is to monitor the population mean and coefficient of variation of the latex population. However, if the laser lens accumulates dirt or other debris which obscures the laser beam signal, the prior art practice has permitted obscuring the alignment problem by increasing the gain of the laser to overcome the interference to the laser beam. In addition, the latex particles are not responsive to the reagents that are used in the instrument. Moreover, the latex particles are a separate control product that is required to be run in a calibration mode in the instrument. The latex particles require additional work to be undertaken to monitor instrument's performance. Therefore, it is advantageous to have a single hematological control product that is both responsive to the reagents used in the instrument and provides and indication of the performance of the laser in the instrument.

It has been determined that X-axis alignment is the most sensitive of the axes and produces the greatest affects on a control product's light scatter position and distribution. The rotated light scatter position of the control product is at a maximum when the X axis is properly aligned and the distribution width is at its minimum. As the alignment degrades to slight misalignment and then to gross misalignment, the control product's position in the histogram shifts to the left, the mean value decreases and the rotated light scatter channel distribution widens.

When analyzing fresh blood and having X-axis misalignment, the white cell populations are shifted left (low light scatter) producing a loss of white cells counted and an increase in noise. As misalignment becomes more extreme, the effect on fresh blood analysis is that the subpopulations of leukocytes merge and differentiation is lost.

Y-axis and Z-axis misalignment do not show the same kind of change of position of the white cell population as exhibited by the white blood cells when caused by X-axis misalignment. It has been determined that Z-axis alignment is related to whether the lens is in a proper focal length which will provide the sharpest image. If the Z-axis is misaligned, then the resulting scatterplot will not have clear distinct clusters of leukocytes. More specifically, in a histogram of light scatter versus DC volume, the separation of the populations of lymphocytes and monocytes, from the population of neutrophils will not be distinct. There will be a degradation of the separation of the light scatter peaks of the volume populations. More specifically, there will be a reduction in the individual populations in amplitudes and an increase in the amplitude of the valleys between the populations.

It has been found that the lymphocyte population of the control product provides information to determine low light scatter while the neutrophil population provides information to determine high light scatter. The relationship between the position of these two population monitors system variables that produce both bias and proportional effects on populations position such as laser alignment (bias) and DC, RF and LS gain (proportional) adjustments.

The use of two control parameters can be employed to determine the problem with the laser's operation. The monitoring of the NEUTROPHIL RLS MEAN and the PEAK TO VALLEY RATIO will provide an indication of the performance of the laser and X axis and Z axis alignment. The LYMPHOCYTE RLS MEAN shows sensitivity similar to the NEUTROPHIL RLS MEAN. The NEUTROPHIL RLS MEAN is the neutrophil mean value in the light scatter channel. The LYMPHOCYTE RLS MEAN is the lymphocyte mean value in the light scatter channel. The PEAK TO VALLEY RATIO (PVR) is the ratio of the amplitude of the rotated light scatter signal of the neutrophil population compared to the rotated light scatter signal of the valley formed between the lymphocyte and monocyte populations, and the neutrophil population.

The PVR provides a reliable quality control parameter to be used in a method to determine whether a problem exists with the laser. When using a control product the PEAK TO VALLEY RATIO should meet a threshold number which has been predetermined. If the PVR meets or exceeds this number, the laser is operating optimally. More specifically, a PVR that meets the predetermined number indicates that there is a clear separation of the neutrophil population and lymphocyte and monocyte populations. If the PVR is less than the predetermined number, then there is an indication that a problem with the laser exists.

As previously noted, the prior art practice has permitted increasing the laser gain to compensate for a dirty lens. However, a latex particle control does not provide specific information concerning the misadjustment of the light scatter signal gain when optical interference exists. It has been determined that when the gain adjustment has been improperly increased that the entire neutrophil population position in the rotated light scatter histogram, including the NEUTROPHIL RLS MEAN, is shifted to the right.

In accordance with the method of this invention, the determination of a PVR that is less than the predetermined value, and the NEUTROPHIL RLS MEAN is above the predetermined value, it indicates that the instrument has a problem with either optical interference or X-axis or Z-axis alignment. Therefore, the technician will know to clean the lens and calibrate the laser alignment. In addition, it has also been determined that if the determination of a PVR that is less than the predetermined value, and the NEUTROPHIL RLS MEAN is below the predetermined value, it indicates that the instrument has a problem with either optical interference which has not been compensated by increasing the gain or X-axis or Z-axis alignment. Moreover, if the PVR is within the predetermined value and the NEUTROPHIL RLS MEAN is either greater than or less than the predetermined value, it indicates that the laser gain is set improperly. Still further, if the PVR is below the predetermined value and the NEUTROPHIL RLS MEAN is within the predetermined value, it indicates that the laser needs replacing because it is losing power.

While the foregoing specification explains the use of some of the control parameters to determine whether an instrument is performing according to manufacturer's specification and the use of the control parameter to diagnose the cause of the malfunction, Table 1 provides a detailed analysis of which control parameters can be used for a control product or for a statistically significant value of patient blood samples to detect and diagnose problems with an instrument's system. In this Table, the following abbreviations are used:

s=sensitivity for the applicable instrument function
SD=standard deviation
OP=opacity
x=measurement of Control Product or Sample

TABLE 1

| Cell/Type | Control Parameter | Control Product | Patient Blood Sample | Lysis | Flow | Alignment | Gain | Chemistry |
|---|---|---|---|---|---|---|---|---|
| Neutrophil | DC Mean | x | x | | | | s | s |
| | DC SD | x | x | | | | s | |
| | RLS Mean | x | x | | | s | s | |
| | RLS SD | x | x | | | s | s | |
| | OP Mean | x | x | | | | s | |

TABLE 1-continued

| Cell/Type | Control Parameter | Control Product | Patient Blood Sample | Lysis | Flow | Alignment | Gain | Chemistry |
|---|---|---|---|---|---|---|---|---|
| | OP SD | x | x | | | | s | |
| | PVR | x | | | | s | | |
| Lymphocyte | DC Mean | x | x | | | | s | |
| | DC SD | x | x | | | | s | |
| | RLS Mean | x | x | | | s | s | |
| | RLS SD | x | x | | | s | s | |
| | OP Mean | x | x | | | | s | |
| | OP SD | x | x | | | | s | |
| | PVR | x | | | | s | | |
| Monocyte | DC Mean | x | x | | | | s | |
| | DC SD | x | x | | | | s | |
| | RLS Mean | x | x | | | s | s | |
| | RLS SD | x | x | | | s | s | |
| | OP Mean | x | x | | | | s | |
| | OP SD | x | x | | | | s | |
| Latex Particle | DC Mean | x | x | | | | s | |
| Sample | DC SD | x | x | | | | s | |
| Analysis | RLS Mean | x | x | | | | s | |
| Mode | RLS SD | x | x | | | s | s | |
| | OP Mean | x | x | | | | s | |
| | OP SD | x | x | | | | s | |
| Noise | COUNT RATIO | x | x | s | | s | | s |
| Flow | WHITE TIME | x | x | | s | | | |

In addition, a latex, polystyrene or other plastic bead can be added to the control product to provide a single reference control product that can further indicate instrument performance. More specifically, the use of this type of control product with the control parameters can provide information about the instruments performance. For example, if the latex particle DC gain is within specification, but the control product has a DC mean not within specification, then there is an indication that there is a problem with the reagent pump volumes.

When this type of control product is used in an instrument that uses VCS technology, the above described example would indicate that there is a problem with the lytic or quench reagent volumes. More specifically, in the VCS type instrument, if the latex particle DC gain is within specification, but the control product has a DC mean that is above the manufacturer's specification, then there is an indication that the lytic reagent volume can be above the optimum level or the quench reagent volume can be below the optimum level. Still further in the VCS example, if the latex particle DC gain is within specification, but the control product has a DC mean that is below the manufacturer's specification, then there is an indication that the lytic reagent volume can be below the optimum level or the quench reagent volume can be above the optimum level.

The process for preparing leukocyte analogs for use in the method of this invention is hereinafter provided in the Examples. Example 1 is a specific example of preferred reagents and techniques for treating goose cells, it being understood that the formulations are only illustrative of those that can be used in the method of this invention. Examples 2, 3 and 4 are specific examples of preferred reagents and techniques for treating the alligator cells, it being understood that the formulations are only illustrative of those that can be used in the method of this invention. Example 5 shows an example of using human white blood cells to produce five subpopulations of leukocyte analogs, it being understood that the formulations are only illustrative of those that can be used in the method of this invention. Example 6 shows an assembly of the four leukocyte populations. It should be appreciated that these Examples provide formulations for the leukocyte analogs which are only illustrative. The reagents and/or techniques described can also be applicable to blood cells from animals other than geese and alligators. Other ingredients and proportions can be employed, in accordance with this disclosure.

EXAMPLE 1

Lymphocyte Analog from Goose Red Blood Cells

The following is a specific example of preferred reagents and recommended specific procedural steps for treating goose red blood cells to obtain a normal sized lymphocyte analog. It will be understood that the formulations and the procedures only are illustrative and that other ingredients, proportions and procedures can be employed, in accordance with the disclosures in this invention.

Phosphate Buffered Saline Solution (PBS) Liter Formulation

1. Sodium phosphate monobasic: 0.2 g
2. Sodium phosphate dibasic.$7H_2O$:2.0 g
3. Sodium azide: 0.1 g
4. Sodium chloride: 9.4 g
5. q.s. to 1 liter with distilled water: pH approximately 7.4; osmolality 315 to 345 mOsm/kg.

Lymphocyte Hypotonic Solution

1. Sodium phosphate monobasic: 0.2 g
2. Sodium phosphate dibasic.$7H_2O$:2.0 g
3. q.s. to 1 liter with distilled water: pH approximately 7.8; osmolality 15 to 25 mOsm/kg.

Procedure

1. Select avian red blood cells having a mean cell volume range of about 140 to 170 fL. Wash the packed avian red blood cells with the phosphate buffered saline solution (PBS).
2. Add 1.0 to 5.0 milligrams of cholesterol to a cell count of $2 \times 10^6$ per microliter and incubate for 2 to 6 hours, at room temperature.

3. Prepare a glutaraldehyde fixative reagent having a glutaraldehyde content of about 0.1 to 0.8% by adding a commercial 25% glutaraldehyde product to the chilled Lymphocyte Hypotonic Solution. Preferably, the temperature is from 2° to 8° C. The preferred concentration of glutaraldehyde is approximately 0.35%.
4. Add the washed red blood cells to a measured amount of the fixative of step 3 at a 1:35 dilution. Transfer to sealed containers which are rolled slowly for 18 to 24 hours at 2° to 8° C. The reduction in hemoglobin content is calculated to be approximately 60% by weight.
5. Remove the supernatant fluid, wash cells several times with the PBS, then resuspend in a suitable storing solution.
6. For a stand alone lymphocyte analog, resuspend the washed fixed cells in the suspension media of this invention and adjust the concentration to simulate that of human lymphocyte cells in normal human blood.
7. For multiple hematological parameters for a control product, add the washed fixed cells in the suspension media of this invention with other hematological compositions and analogs desired for the multiple parameter hematology control product, the cell count being appropriate to measure lymphocyte proportions.
8. With suitable stabilizers, the fixed cells can be stored for a time period in excess of six months.

In accordance with the above example, but starting with other types of mammalian red blood cells, comparable results are obtained.

EXAMPLE 2

Monocyte Cell Analog from Alligator Red Blood Cells

The following is a specific example of preferred reagents and recommended specific procedural steps for treating alligator red blood cells to obtain the monocyte cell analog. It will be understood that the formulations and the procedures are only illustrative and that other ingredients, proportions and procedures may be employed, in accordance with the disclosures in this invention.

Monocyte Hypotonic Solution

1. Sodium phosphate monobasic: 0.1 g
2. Sodium phosphate dibasic 1.0 g
3. q.s. to 1 liter with distilled water; pH approximately 7.8; osmolality 5 to 15 mOsm/kg.

Washing solution for cells (PBS), as set forth in Example 1.

Procedure

1. Select alligator red blood cells having a mean cell volume range of about 350 to 450 fL. Wash the packed alligator red blood cells with PBS.
2. Add 1.0 to 5.0 milligrams of cholesterol to a cell count of $1\times10^6$ per microliter and incubate 3 to 5 hours at room temperature.
3. Prepare a glutaraldehyde fixing reagent having a glutaraldehyde content of about 0.1 to 0.8% by adding a commercial 25% glutaraldehyde product to the chilled Monocyte Hypotonic Solution. Preferably the temperature is from 2° to 8° C. The preferred concentration of glutaraldehyde is approximately 0.15%.
4. Add the washed red blood cells to a measured amount of the fixative of step 3 at a 1:50 dilution. Transfer to sealed containers which are rolled slowly for 18 to 24 hours at room temperature. The reduction in hemoglobin content is calculated to be approximately 40% by weight.
5. Remove the supernatant fluid, wash cells several times with the PBS, then resuspend in a suitable storing solution.
6. For a stand alone monocyte analog, resuspend the washed fixed cells in the suspension media of this invention and Adjust the concentration to simulate that of human monocyte cells in normal human blood.
7. For multiple hematological control product, add the washed fixed cells in the suspension media of this invention with other hematological compositions and analogs desired for the multiple parameter control product in the appropriate concentration to measure monocyte cells.
8. With suitable stabilizers, the fixed cells can be stored for a time period in excess of six months.

EXAMPLE 3

Eosinophil Analog from Red Blood Cells of the Alligator

The following is a specific example of preferred reagents and recommended specific procedural steps for treating red blood cells of the alligator to obtain the eosinophil analog. It will be understood that the formulations and the procedures are only illustrative, and that other ingredients, proportions and procedures may be employed, in accordance with the disclosures in this invention.

Eosinophil Hypotonic Solution

1. Sodium phosphate monobasic: 0.32 grams
2. Sodium phosphate dibasic 8.08 grams
3. q.s. to 1 liter with distilled water; pH approximately 8.0; osmolality 75 to 85 mOsm/kg.

Eosinophil Hemoglobin Denaturing Treatment Solution 1. dimethyldicocoammonium chloride 2.5 grams
2. tris(hydroxymethyl)amino methane 6.06 grams (organic buffer)
3. q.s. to 1 liter with distilled water: pH approximately 10.5.

Eosinophil Post-Treatment Wash Solution 1. polyoxethylated alkylphenol 5 grams (Diazopan® SS-837 by GAF Chemical Corp.)
2. q.s. to 1 liter with distilled water Washing solution for cells (PBS), as set forth in Example 1.

Procedure

1. Select alligator red blood cells having a mean cell volume range of about 400 to 500 fL. Wash the packed alligator red blood cells with PBS.
2. Add 0.25 to 1.25 milligrams of cholesterol to a cell count of $1\times10^6$ per microliter and incubate 2 to 5 hours, at room temperature.
3. Prepare a glutaraldehyde cross linking reagent having a glutaraldehyde content of about 0.1 to 0.8% by adding a commercial 25% glutaraldehyde product to the Eosinophil Hypotonic Solution. The preferred concentration of glutaraldehyde is approximately 0.2%.
4. Add the washed red blood cells to a measured amount of the cross linking of step 3 at a 1:50 dilution. Transfer to sealed containers which are rolled slowly for 18 to 24 hours at room temperature.

5. Remove the supernatant fluid, wash cells several times with the PBS.
6. Add the washed red blood cells to the Eosinophil Hemoglobin Denaturing Treatment Solution at a 1:10 dilution. Transfer to sealed containers which are rolled slowly for 2–4 hours at room temperature.
7. Remove the supernatant fluid, wash cells several times with the Eosinophil Post-Treatment Wash Solution to remove the Eosinophil Hemoglobin Denaturing Treatment Solution. Then resuspend in a suitable storage solution.
8. For a stand alone eosinophil analog, resuspend the washed fixed cells in the suspension media of this invention and adjust the concentration to simulate that of human eosinophil cells in normal human blood.
9. For multiple hematological control products, add the washed fixed cells in the suspension media of this invention with other hematological compositions and analogs desired for the multiple parameter control product in the appropriate concentration to measure eosinophil cells.
10. With suitable stabilizers, the fixed cells can be stored for a time in excess of six months.

EXAMPLE 4

Neutrophil Cell Analog from Alligator Red Blood Cells

The following is a specific example of preferred reagents and recommended specific procedural steps for treating alligator red blood cells to obtain the monocyte cell analog. It will be understood that the formulations and the procedures are only illustrative and that other ingredients, proportions and procedures may be employed, in accordance with the disclosures in this invention.

Neutrophil Hypotonic Solution

1. Sodium phosphate monobasic: 0.23 g
2. Sodium phosphate dibasic 5.32 g
3. q.s. to 1 liter with distilled water; pH approximately 8.0; osmolality 45 to 65 mOsm/kg.

Washing solution for cells (PBS), as set forth in Example 1.

Procedure

1. Select alligator red blood cells having a mean cell volume range of about 400 to 500 fL. Wash the packed alligator red blood cells with PBS.
2. Prepare a glutaraldehyde fixing reagent having a glutaraldehyde content of about 0.1 to 0.8% by adding a commercial 25% glutaraldehyde product to the Neutrophil Hypotonic Solution. The preferred concentration of glutaraldehyde is approximately 0.4%.
3. Add the washed red blood cells at a count of $1 \times 10^6$ to a measured amount of the fixative of step 3 at a 1:50 dilution. Transfer to sealed containers which are rolled slowly for 18 to 24 hours at room temperature.
4. Remove the supernatant fluid, wash cells several times with the PBS, then resuspend in a suitable storing solution.
5. Add packed cells to a nonionic surfactant solution. Said solution tends to standardize the volume of donor cells. The solution comprises 0.5 grams of octylphenoxy polyethoxy ethanol having an HLB of approximately 13.5 (Triton® X-100 by Rohm and Haas Co.,) in 1 liter of distilled water.
6. Remove the supernatant fluid, wash cells several times with the PBS, then resuspend in a suitable storing solution.
7. For a stand alone neutrophil analog, resuspend the washed fixed cells in the suspension media of this invention and adjust the concentration to simulate that of human neutrophil cells in normal human blood.
8. For multiple hematological control product, add the washed fixed cells in the suspension media of this invention with other hematological compositions and analogs desired for the multiple parameter control product in the appropriate concentration to measure neutrophil cells.
9. With suitable stabilizers, the fixed cells can be stored for a time period in excess of six months.

EXAMPLE 5

Five Subpopulations of Leukocyte Analogs from Human White Blood Cells

1. Add whole blood to a Dextran (molecular weight 100,000 to 500,000) solution at a dilution of 1:10 and allow to settle by gravity means for 1 to 3 hours.
2. Remove the supernatant, which includes the white blood cells, platelets and some residual red blood cells.
3. Centrifuge the product of step 2 at less than 300 RCF for about 10 minutes. Aspirate the platelets leaving the button of white blood cells, residual red blood cells, and a small amount of plasma with which to resuspend the cells.
4. Add a suitable lytic agent, such as water, to lyse the red blood cells from the white blood cells.
5. Centrifuge the product of step 4 and remove supernatant, leaving packed white blood cells. Resuspend the packed white blood cells in an approximately equal volume of saline solution.
6. Add white blood cells to a suitable isoosmotic fixative solution, such as 5% formaldehyde and 95% PBS (volume percent), in a 1:10 dilution and transfer to sealed containers which are rolled slowly for 18–30 hours at room temperature.
7. Add a glutaraldehyde fixative solution having approximately a 0.1% concentration of glutaraldehyde at a 1:1 dilution to the pool, and continue fixation for an additional 8–12 hours.
8. Remove the supernatant fluid, wash cells several times with the PBS, then resuspend in a suitable storing solution.
9. For stand alone five subpopulation leukocyte analogs assembly, resuspend the washed fixed cells in the suspension media of this invention and adjust the concentration to simulate that of human leukocyte cells in normal human blood.
10. For multiple hematological control product, add the washed fixed cells in the suspension media of this invention with other hematological compositions and analogs desired for the multiple parameter hematology control product, the cell count being appropriate to measure leukocytes proportions.
11. With suitable stabilizers, the fixed cells can be stored for a time period in excess of six months.

EXAMPLE 6

In a sub-assembly for simulating the targeted composition of white blood cells in a normal human blood sample, the following quantities of the individual components are employed:

|         |           |                         | STOCK SOLUTION       |
|---------|-----------|-------------------------|----------------------|
| 0.150 L | Example 1 | lymphocytes             | 500 × $10^3$/uL      |
| 0.040 L | Example 2 | monocytes               | 500 × $10^3$/uL      |
| 0.030 L | Example 3 | eosinophils             | 500 × $10^3$/uL      |
| 0.280 L | Example 4 | neutrophils             | 500 × $10^3$/uL      |
| 0.500 L | diluent   | phosphate buffered saline |                    |

In the final assembly of the four leukocyte populations, remove the supernatant fluid, then resuspend the cells in 1.0 liter of an aqueous solution of Moducyte® having a final concentration of 800 milligrams of cholesterol.

This assembly can be stored for up to about six months with the addition of known suitable stabilizers.

The ratio and total cell count for the leukocytes populations can be adjusted to represent pathological, as well as normal conditions in human blood. These compositions are useful likewise in control and calibrator products particularly for automated particle analysis instruments employing the Coulter Principle. In addition, latex particles can be added to the control product to provide a single control product that can further indicate instrument performance.

Suspensions of untreated human red blood cells, simulated white blood cells, and stabilized or simulated platelets can be thereafter added in such proportion that the final red blood cell, white blood cell and platelet counts, as well as hemoglobin content and hematocrit fall in the desired range.

Stabilized platelets are furnished by processes known in the art. Useful processes include:
1. A combination of iodoacetamide and an iminodiacetic acid or salt thereof, together with a compatible bacteriostatic agent in an aqueous solution which is maintained at a preselected range of pH and osmolality as is described in U.S. Pat. No. 4,405,719.
2. A fixative-stabilizing composition containing a glutaraldehyde concentration of 0.1% to 5% and a non-ionic surfactant which is a mixture of ethoxylates of certain isomeric linear alcohols, as is more fully described in U.S. Pat. No. 4,389,490.
3. A human platelet analog comprising goat erythrocytes stabilized, combined and blended as necessary to have a size range and volume distribution close to that of human platelets, as is described in U.S. Pat. No. 4,264,470.

The values for each of the hematological parameters can be varied to represent abnormal low and abnormal high conditions. The white blood cell count in normal blood is 5,000 to 11,000 per microliter (uL) with a lymphocyte value of 20 to 40%, mononuclear cell value of less than 10%, a granulocyte value of 60 to 80%, eosinophil value less than approximately 5%, and basophil value less than approximately 2%. The normal range in human blood for red blood cells is 4,000,000 to 5,000,000 cells per microliter. The normal hemoglobin value is 12 to 16 grams/100 ml. The term "hematocrit" is defined as the ratio of volume of packed red blood cells to the volume of whole blood. The normal ratio in humans is about 45%. The mean corpuscular volume is the ratio of the volume of packed red blood cells in ml per liter of blood to red blood cells in millions per microliter. The mean corpuscular hemoglobin concentration is an index indicating the mean or average weight of hemoglobin per 100 ml of packed red blood cells in terms of percent. The mean corpuscular hemoglobin is the ratio of hemoglobin content, in grams per liter, to red blood cells, in millions per microliter.

While in the foregoing specification, a detailed description of the invention has been set down for the purpose of illustration, many variations in the details herein give may be made by those skilled in the art without departing from the spirit and scope of the invention.

We claim:

1. A reference control composition for hematology instruments comprising:

a) a multiplicity of white blood cell analogs comprising fixed red blood cells, suspended in b) an aqueous suspension medium comprising a lipoprotein;

wherein said lipoprotein comprises at least one of cholesterol, cholesterol esters, cholesterol combined with phospholipids, cholesterol combined with albumin and cholesterol esters combined with albumin;

wherein said analogs simulate populations of lymphocytes, monocytes, neutrophils, and eosinophils in human blood; and wherein populations of said analogs can be distinguished in a hematology instrument according to measurements of their D.C. (volume) and light scatter characteristics.

2. The reference control composition of claim 1, wherein the suspension medium contains from 400 to 1,200 mg per liter of cholesterol.

3. The reference control composition of claim 1, wherein the lipoprotein comprises high density lipoprotein.

4. The reference control composition of claim 1, further comprising lysable red blood cells.

5. The reference control composition of claim 4, further comprising simulated platelets.

6. A method of making a reference control composition for hematology instruments comprising:

suspending a multiplicity of white blood cell analogs derived from fixed red blood cells in an aqueous suspension medium comprising a lipoprotein;

wherein said lipoprotein comprises at least one of cholesterol, cholesterol esters, cholesterol combined with phospholipids, cholesterol combined with albumin and cholesterol esters combined with albumin; and wherein said analogs simulate populations of lymphocytes, monocytes, neutrophils, and eosinophils in human blood; and wherein populations of said analogs can be distinguished in a hematology instrument according to measurements of their D.C. (volume) and light scatter characteristics.

7. A method for determining the accuracy of a hematology instrument comprising:

a) providing an instrument that is capable of measuring five populations of leukocytes in human blood, b) providing a reference control composition comprising a multiplicity of white blood cell analogs comprising fixed red blood cells, suspended in an aqueous suspension medium comprising a lipoprotein;

wherein said lipoprotein comprises at least one of cholesterol, cholesterol esters, cholesterol combined with phospholipids, cholesterol combined with albumin and cholesterol esters combined with albumin;

wherein said analogs simulate populations of lymphocytes, monocytes, neutrophils, and eosinophils in human blood; and;

wherein populations of said analogs can be distinguished in a hematology instrument according to measurements of their D.C. (volume) and light scatter characteristics; and c) passing the reference control composition through the hematology instrument to provide a five-part differential readout exhibiting populations corresponding to at least lymphocytes, monocytes, neutrophils, and eosinophils.

8. The method of claim 7, wherein said readout exhibits a population corresponding to basophils.

* * * * *

UNITED STATES PATENT AND TRADEMARK OFFICE
CERTIFICATE OF CORRECTION

PATENT NO.    : 6,362,003 B1
DATED         : March 26, 2002
INVENTOR(S)   : Young et al.

It is certified that error appears in the above-identified patent and that said Letters Patent is hereby corrected as shown below:

<u>Title page,</u>
Item [75], Inventors, "Cooper, both of FL" should read -- Cooper City, both of FL --.

Signed and Sealed this

Thirteenth Day of May, 2003

JAMES E. ROGAN
*Director of the United States Patent and Trademark Office*

UNITED STATES PATENT AND TRADEMARK OFFICE
CERTIFICATE OF CORRECTION

PATENT NO. : 6,362,003 B1
DATED : March 26, 2002
INVENTOR(S) : Young et al.

It is certified that error appears in the above-identified patent and that said Letters Patent is hereby corrected as shown below:

Title page,
Item [63], Related U.S. Application Data, should read -- Continuation of application Nos. 09/152,262, filed on September 14, 1998, 09/172,122, filed on October 14, 1998, now abandoned, and 09/273,358, filed March 22, 1999, now abandonded, which ae continuations of application No. 08/787,408, filed on January 22, 1997, which is a continuation of application No. 08/432, 435, filed on April 28, 1995, now abandoned, which is a continuation-in-part of application No. 08/386,711, filed on February 8, 1997, now Pat. No. 5,529,933, which is a continuation of application No. 08/081,529, filed on June 23, 1993, now abandoned, which is a continuation of application No. 07/840,438, filed on February 24, 1992, now abandoned --

Signed and Sealed this

Seventh Day of September, 2004

JON W. DUDAS
*Director of the United States Patent and Trademark Office*